US011202890B2

(12) United States Patent
Kanner et al.

(10) Patent No.: US 11,202,890 B2
(45) Date of Patent: Dec. 21, 2021

(54) ACTUATING MECHANISM, METHOD OF OPERATION AND ASSEMBLY FOR FLUID DISPLACEMENT AND PRESSURIZING DEVICE

(71) Applicant: Atrion Medical Products, Inc., Arab, AL (US)

(72) Inventors: Rowland W. Kanner, Guntersville, AL (US); Brian A. Roberts, Owens Cross Roads, AL (US)

(73) Assignee: ATRION MEDICAL PRODUCTS, INC., Arab, AL (US)

( * ) Notice: Subject to any disclaimer, the term of this patent is extended or adjusted under 35 U.S.C. 154(b) by 727 days.

(21) Appl. No.: 15/442,146

(22) Filed: Feb. 24, 2017

(65) Prior Publication Data

US 2017/0246433 A1    Aug. 31, 2017

Related U.S. Application Data

(60) Provisional application No. 62/299,860, filed on Feb. 25, 2016.

(51) Int. Cl.
| | |
|---|---|
| *A61M 25/10* | (2013.01) |
| *A61M 39/10* | (2006.01) |
| *A61M 5/48* | (2006.01) |
| *A61M 5/315* | (2006.01) |
| *A61B 17/88* | (2006.01) |

(52) U.S. Cl.
CPC ........... *A61M 25/10182* (2013.11); *A61M 25/10187* (2013.11); *A61B 17/8822* (2013.01); *A61B 17/8833* (2013.01); *A61M 5/3158* (2013.01); *A61M 5/31581* (2013.01); *A61M 5/486* (2013.01)

(58) Field of Classification Search
CPC ...... A61M 25/10182; A61M 25/10187; A61M 25/10188; A61M 2205/3331; A61M 5/486; A61M 5/3158; A61M 5/31581; A61M 5/31501; A61M 2005/31508; A61B 17/8822; A61B 17/8833
See application file for complete search history.

(56) References Cited

U.S. PATENT DOCUMENTS

| | | | |
|---|---|---|---|
| 4,333,456 A * | 6/1982 | Webb | A61M 5/24 604/121 |
| 4,838,864 A | 6/1989 | Peterson | |
| 5,019,041 A * | 5/1991 | Robinson | A61M 25/104 604/100.02 |

(Continued)

FOREIGN PATENT DOCUMENTS

WO    2009023913 A1    2/2009

*Primary Examiner* — William R Carpenter
*Assistant Examiner* — William R Frehe
(74) *Attorney, Agent, or Firm* — Clark Hill PLC; James R. Foley

(57) ABSTRACT

A fluid pressurizing and displacement device which is configured for both macro movement and micro movement of a plunger. In order to execute micro movement of the plunger, a user need only rotate the plunger; to execute macro movement of the plunger, a user need only push or pull the plunger. This simplicity in use is possible because a half-nut (or other suitable structure within the device) remains engaged with the plunger, except when the plunger is being pushed or pulled by its operator. All user motions are simple and intuitive.

16 Claims, 30 Drawing Sheets

(56) References Cited

U.S. PATENT DOCUMENTS

| | | | |
|---|---|---|---|
| 5,137,514 A * | 8/1992 | Ryan | A61M 25/104 |
| | | | 604/99.01 |
| 5,209,732 A | 5/1993 | Lampropoulos et al. | |
| 5,634,910 A * | 6/1997 | Kanner | A61M 25/10182 |
| | | | 604/208 |
| 5,752,935 A | 5/1998 | Robinson et al. | |
| 6,106,496 A * | 8/2000 | Arnissolle | A61M 25/10182 |
| | | | 604/97.01 |
| 6,156,050 A | 12/2000 | Davis et al. | |
| 7,604,618 B2 | 10/2009 | Dixon et al. | |
| 7,717,880 B2 | 5/2010 | Denolly | |
| 8,499,681 B2 | 8/2013 | Kanner et al. | |
| 9,084,873 B2 | 7/2015 | Lampropoulos et al. | |
| 2004/0122361 A1* | 6/2004 | Hart | A61M 25/10184 |
| | | | 604/97.02 |
| 2004/0260237 A1 | 12/2004 | Squadrito | |
| 2013/0123693 A1* | 5/2013 | Lampropoulos | |
| | | | A61M 25/10181 |
| | | | 604/97.02 |
| 2014/0343490 A1 | 11/2014 | Kanner et al. | |
| 2015/0051543 A1* | 2/2015 | Chadwick | A61M 25/10182 |
| | | | 604/97.02 |
| 2017/0209197 A1* | 7/2017 | Balbierz | A61B 17/8816 |
| 2018/0326145 A1* | 11/2018 | Jiang | A61M 5/1452 |
| 2020/0229855 A1* | 7/2020 | Purdy | A61B 17/8822 |

* cited by examiner

US 11,202,890 B2

ACTUATING MECHANISM, METHOD OF OPERATION AND ASSEMBLY FOR FLUID DISPLACEMENT AND PRESSURIZING DEVICE

RELATED APPLICATIONS (PRIORITY CLAIM)

This application claims the benefit of U.S. Provisional Application Ser. No. 62/299,860, filed Feb. 25, 2016, which is hereby incorporated herein by reference in its entirety.

BACKGROUND

The present invention generally relates to fluid pressurizing devices, such as syringe devices for use in inflating and deflating a catheterized balloon.

Fluid pressurization devices adapted for selectively applying and relieving a measured pressure on a closed volume of fluid have been developed for use in inflation and deflation of a balloon catheter used in angioplasty balloon procedures interiorly of blood vessels, or other types of balloon catheterization procedures. Fluid pressurizing devices for this purpose generally provide for high-volume fluid displacement, and include a plunger screw which is attached to a large piston. The devices employ a nut mechanism to provide the necessary mechanical advantage for creating elevated pressures, wherein plunger loadings upon the piston can exceed 500 lbF.

Most of these types of devices require an overt and willful action by users of these devices in order to select the desired plunger screw and nut engagement position. For example, U.S. Pat. No. 4,838,864 discloses one such device—a syringe device for use in inflating and deflating a catheterized balloon. The device uses a manually operated screw plunger to achieve or maintain specific balloon pressure, and the pressure is monitored using an associated pressure gauge. To release the plunger for macro movement (i.e., quick advancement or withdrawal of the plunger), a spring-biased button must be pressed by the user so that a partial thread disengages the screw plunger. When the spring-biased button is released, the partial thread re-engages the screw plunger.

Similarly, each of the devices disclosed in U.S. Pat. Nos. 5,752,935 and 7,717,880 and 8,499,681 utilize a half-nut arrangement, wherein a half-nut selectively engages and disengages the threaded plunger. When a user of the device wants to execute a macro movement of the plunger (either forward or backward), the user moves a lever which causes the half-nut to disengage from the threaded plunger, thereby allowing macro movement of the plunger. The user moves the lever back to its original position in order to re-engage the half-nut with the threaded plunger.

U.S. Pat. Nos. 5,209,732 and 9,084,873 each disclose a syringe device which utilizes a long, externally threaded spline that is slidable within a plunger which carries a piston. This spline engages with an internally threaded nut section attached to the syringe body, in order to provide the mechanical advantage of a screw mechanism that is necessary for building high pressure within the device. Disengagement of the threaded spline to allow free movement of the plunger is accomplished in both devices by withdrawing the spline longitudinally rearward and down within the plunger. In the instance of U.S. Pat. No. 5,209,732, a T-handled lever attached to the threaded spline can be directly withdrawn at the user's discretion if he first closes his hand tightly about both the plunger and spline T-handle assembly to withdraw the spline's T-handle into the plunger's handle which, in turn, draws the attached spline down into the plunger. In the instance of U.S. Pat. No. 9,084,873, the operation is similar; however, withdrawal of the threaded spline to cause its release from the engaged nut is accomplished when a user rotates the T-handle in a traverse direction relative to the longitudinal axis of the plunger shaft. This action allows a linkage, connected to the threaded spline, to withdraw the spline longitudinally rearward and down into the plunger.

Regardless of the plunger control mechanism employed by any of the aforementioned devices, all have a need to also be operable freely and independently from their threaded engagement means in order to allow rapid gross movement (i.e., macro movement) of their plungers for quickly drawing working fluid into their syringe bodies and to purge unwanted air out during preparation for a balloon procedure. Additionally, the plungers must also be able to be rapidly withdrawn backward in order to create a vacuum within the syringe body to quickly deflate and purge a previously inflated catheter mounted balloon. In all examples of patented devices previously discussed, taking each one through a full round of filling, purging air, pressurization, depressurization and purging a catheter mounted balloon demands that their user willfully press a button, move a lever, squeeze a handle, or manipulate a handle in a transverse direction, in order to select the next desired operating mode (i.e., to enable the device for macro movement of the plunger, as opposed to allowing only micro movement of the plunger). In other words, in each of the prior art devices described hereinabove, micro movement of the plunger is the default configuration, and then in order to have the device allow macro movement of the plunger, a user must perform an overt act with regard to a button, lever or handle of the device.

SUMMARY

An object of an embodiment of the present invention is to provide a fluid pressurizing device that has an improved mechanism for actuating a screw plunger that is both easy and very intuitive for users to operate.

Another object of an embodiment of the present invention is to provide a method of operating and assembling such a device.

Briefly, an embodiment of the present invention provides a fluid pressurizing and displacement device which is configured such that a user merely withdraw a plunger in order to fill the device with fluid, and press the plunger forward in order to purge the device of unwanted air or fluid. When the device is filled with fluid, the plunger can either be rapidly advanced forward to allow quick balloon filling, or the user can just begin rotating the plunger handle (such as in a clockwise direction) in order to create high balloon pressures by utilizing the mechanical advantage through use of the engaged plunger thread. Alternatively, the plunger can either be rapidly pulled back to allow quick deflation of the balloon, or the user can just begin rotating the plunger handle (such as in a counter-clockwise direction) in order to slowly reduce the fluid pressure in the balloon. In other words, to execute micro movement of the plunger, a user need only rotate the plunger; to execute macro movement of the plunger, a user need only push or pull the plunger. This simplicity in use is possible because a half-nut (or other suitable actuating mechanism within the device) remains engaged with the plunger, except when the plunger is being pushed or pulled by its operator. All user motions are simple and intuitive, involving only pulling, pushing or rotating the plunger.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which.

DESCRIPTION OF ILLUSTRATED EMBODIMENTS

Figure 1:
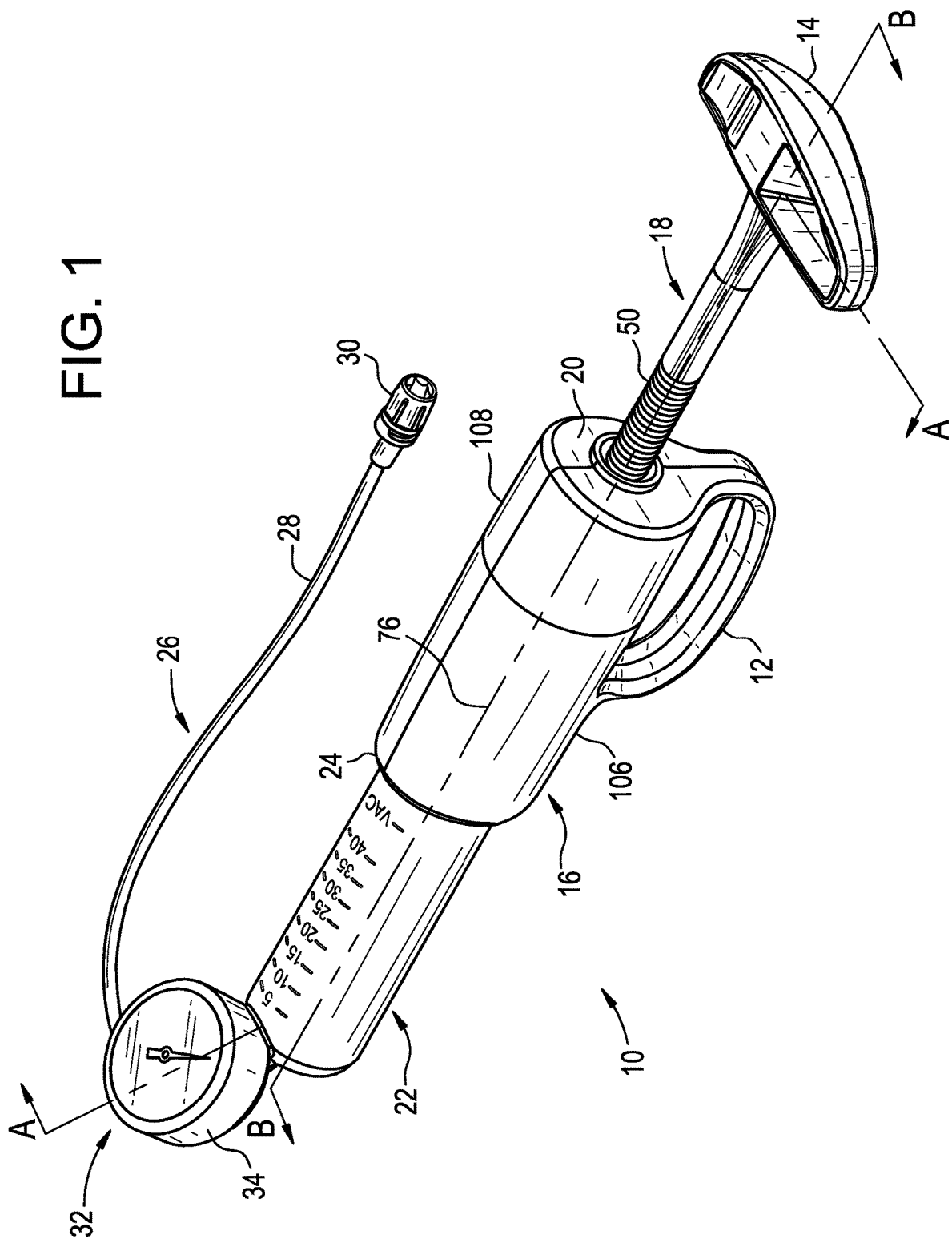
FIG. 1 is a perspective view of a fluid displacement and pressurizing device which is in accordance with a first embodiment of the present invention.

While this invention may be susceptible to embodiment in different forms, there are shown in the drawings and will be described herein in detail, specific embodiments with the understanding that the present disclosure is to be considered an exemplification of the principles of the invention, and is not intended to limit the invention to that as illustrated.

FIG. 1 illustrates a fluid displacement and pressurizing device 10 which is in accordance with an embodiment of the present invention. The device 10 is simple, easy to use, easy to assemble, and comprises very few parts.

The device 10 includes a handle loop 12, or other type of grip structure, for engagement by a user using one hand, and a handle which a user can push, pull or twist using the other hand. All user motions are simple and intuitive, involving only pulling, pushing or rotating the handle 14 while holding onto the handle loop 12.

The device 10 comprises a user grip assembly 16, and a plunger 18 extends from one end 20 of the user grip assembly 16. A syringe body 22 extends from the other end 24. The syringe body 22 is configured to be engaged with a hose assembly 26 or the like, which may include a hose 28 and a Luer connector 30 at the end of the hose 28, ultimately for connection to a device such as a catheterization balloon to be pressurized, etc. by the device 10.

A pressure gauge 32 is preferably provided, for indicating the fluid pressure inside the device 10. The pressure gauge 32 may be retained in an integral housing 34 which is part of the syringe body 22. Alternatively, the pressure gauge 32 may extend from the syringe body 22, threaded into a threaded bore provided on the syringe body 22. The syringe body 22 includes a passageway 36 which provides communication between the gauge 32 and a pressure chamber 46 inside the syringe body 22.

The user grip assembly 16 provides the handle loop 12 (or other type of grip structure) for engagement by a user using one hand, and the plunger 18 preferably includes the handle 14 which a user can push, pull or twist using the other hand.

The device 10 is configured such that a user merely pulls on the handle 14 of the plunger 18 in order to fill the device 10 with fluid, and presses the handle 14 of the plunger 18 forward in order to purge the device 10 of unwanted air or fluid. When the device 10 is filled with fluid, the user can rapidly push the handle 14 of the plunger 18 forward to fill the balloon (for example) quickly, or the user can just begin rotating the handle 14 of the plunger 18 (such as in a clockwise direction) in order to slowly add pressure to the balloon. Alternatively, the user can pull the handle 14 of the plunger 18 back rapidly to quickly deflate the balloon, or the user can just begin rotating the handle 14 of the plunger 18 (such as in a counter-clockwise direction) in order to slowly reduce the fluid pressure in the balloon.

In other words, to execute micro movement of the plunger 18, a user need only rotate the handle 14 of the plunger 18; to execute macro movement of the plunger 18, a user need only push or pull the handle 14 of the plunger 18. All user motions are simple and intuitive, involving only pulling, pushing or rotating the handle 14 of the plunger 18.

Figure 2:
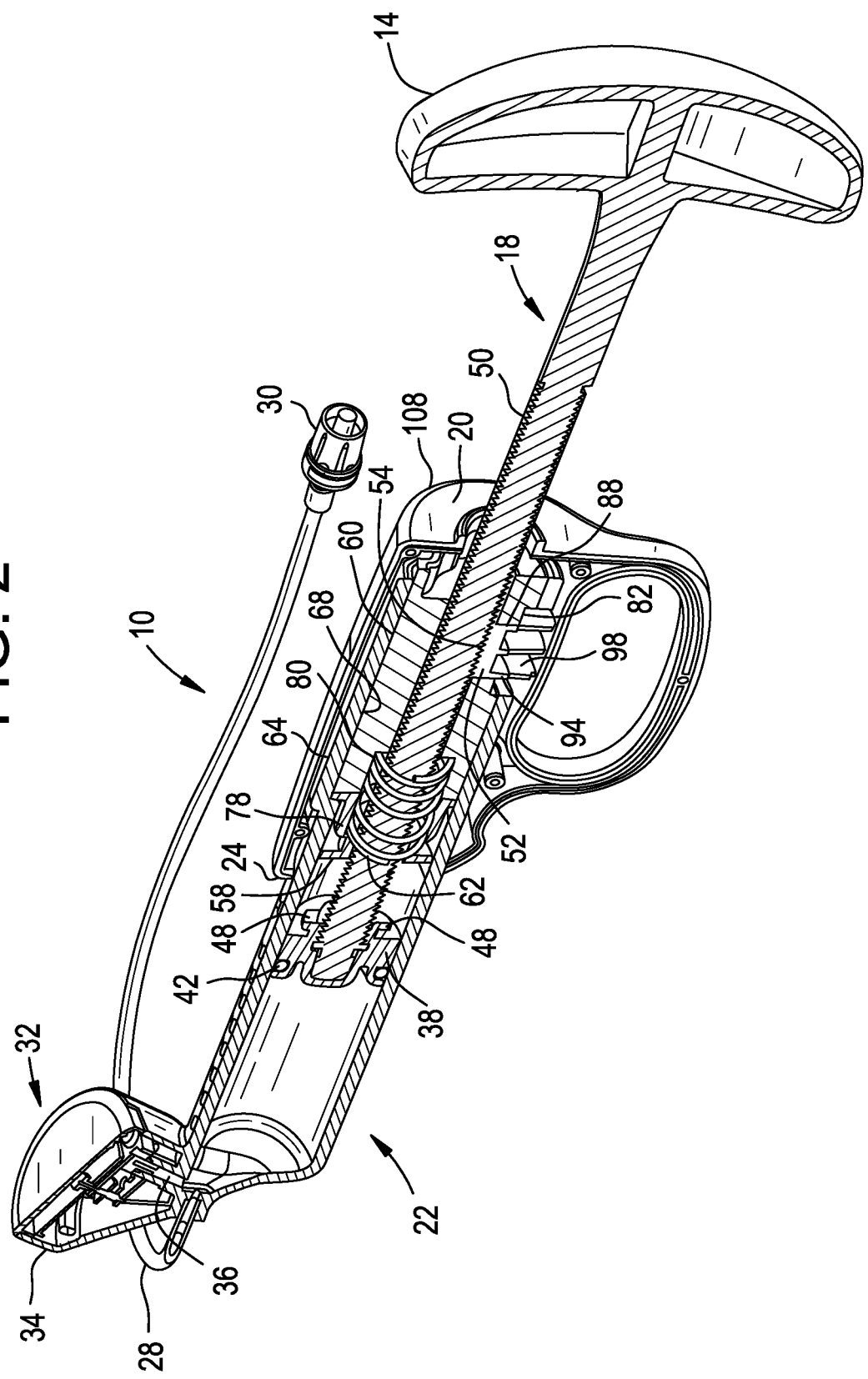
FIG. 2 is a cross-sectional view of the fluid displacement and pressurizing device shown in FIG. 1, taken along line A-A of FIG. 1, showing the device during pressurizing.
Figure 3:
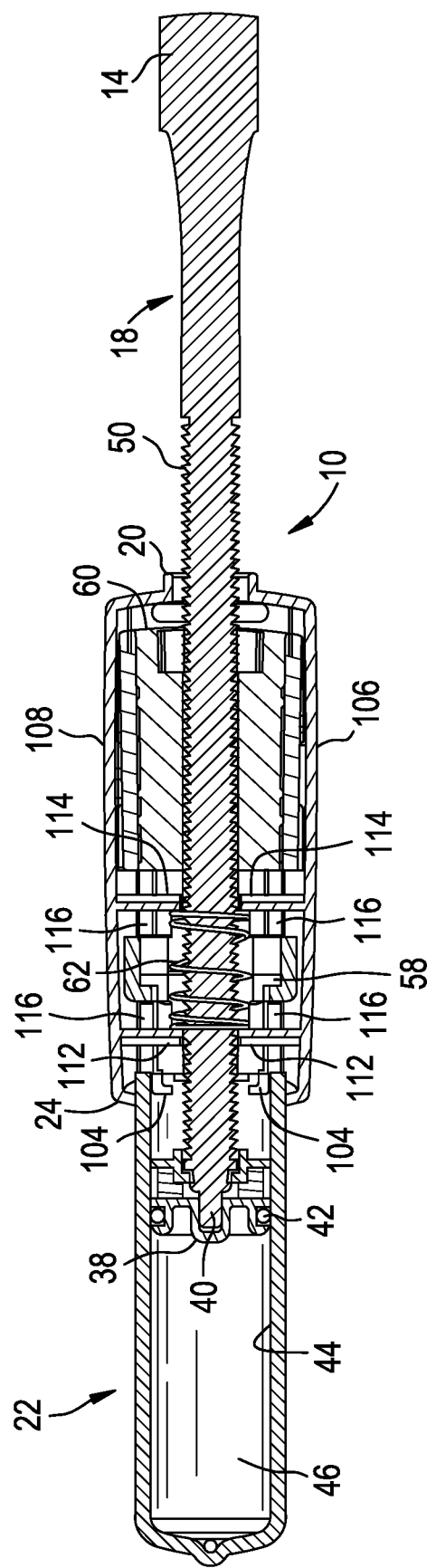
FIG. 3 is a cross-sectional view of the fluid displacement and pressurizing device shown in FIG. 1, taken along line B-B of FIG. 1, showing the device during pressurizing.

FIGS. 2 and 3 provide cross-sectional views in which the internal components of the device can be seen. Specifically, FIG. 2 is a cross-sectional view of the device taken along line A-A of FIG. 1, while FIG. 3 is a cross-sectional view taken along line B-B.

As shown in FIGS. 2 and 3, a piston 38 is engaged with the end 40 of the plunger 18, and at least one piston seal 42 (such as one or more o-rings) is disposed on the piston 38. The piston seal 42 engages an internal wall 44 of the syringe body 22 such that a pressure chamber 46 therein can be pressurized, and fluid is not able to move from the pressure chamber 46, past the piston seal 42. Engagement of the piston 38 with the end 40 of the plunger 18 may be conventional. The piston 38 preferably includes one or more detent ears 48, which will be described in more detail later hereinbelow.

The plunger 18 includes a thread 50 thereon which is configured to engage and disengage a half-nut 52 (or other suitable actuating mechanism) in the device 10. The half-nut 52 has a thread 54 thereon which threadably engages and disengages the thread 50 on the plunger 18. When the half-nut 52 is engaged with the thread 50 on the plunger 18, the plunger 18 can be turned by a user (using the handle 14) to cause the piston 38 to slowly advance or withdraw within the syringe body 22.

A carrier assembly 56, preferably in the form of a front carrier 58, a rear carrier 60, and a centralization spring 62 disposed therebetween, are disposed in the syringe body 22. The plunger 18 extends through the carrier assembly 56 (i.e., through the two carriers 58, 60 and through the centralization spring 62).

The syringe body 22 preferably includes orientation channels 64, 66, such as a top orientation channel 64 and side orientation channels 66, which define a top guide groove 68 and side guide grooves 70, respectively. These guide grooves 68, 70 receive bosses 74 on the front carrier 58 as well as receive alignment tabs 72 on the rear carrier 60, such that the carriers 58, 60 are prevented from rotating in the syringe body 22, and generally define a path for travel of the carrier assembly 56, coaxial with the longitudinal axis 76 of the device 10.

The front carrier 58 includes a spring pocket 78 for receiving one end of the centralization spring 62, and the rear carrier 60 includes a spring pocket 80 for receiving the opposite end of the centralization spring 62. The rear carrier 60 preferably defines a half-nut pocket 82 which receives the half-nut 52. Preferably, the syringe body 22 provides an aperture 84, and the half-nut 52 operates within the aperture 84 and the half-nut pocket 82 in the rear carrier 60.

The half-nut 52 has a thrust surface 86 which engages a corresponding thrust face 88 located in the half-nut pocket 82. The rear carrier 60 also preferably includes latches 90 which engage corresponding latch slots 92 which are provided on the syringe body 22. Thrust from the half-nut 52 is delivered to the rear carrier 60 via interaction between the thrust surface 86 and the thrust face 88. The latches 90 and corresponding latch slots 92 function to provide that the rear carrier 60 can thereafter transfer this trust to the syringe body 22.

In addition to the thrust surface 86, the half-nut 52 preferably includes support ribs 94 which are formed on the bottom 96 of the half-nut 52. These support ribs 94 bear upon buttress elements 98, such as three buttress elements, which are provided inside the user grip assembly 16. As will be described more fully later herein, radial force upon the half-nut 52 (while under load) is resisted by these buttress elements 98 (via engagement with the support ribs 94).

The half-nut 52 also includes cams 100 on each side of the half-nut 52 which engage cam followers 102 which are provided on the interior of the user grip assembly 16. The cams 100 on each side of the half-nut 52 are configured such that the half-nut 52 can move up and down in the half-nut pocket 82 provided in the rear carrier 60, and into and out of threaded engagement with the thread 50 on the plunger 18.

As mentioned briefly above, the piston 38 preferably includes detent ears 48. The detent ears 48 are configured to engage corresponding detent receptacles 104 which are provided on the front carrier 58 of the carrier assembly 56.

Figure 13:
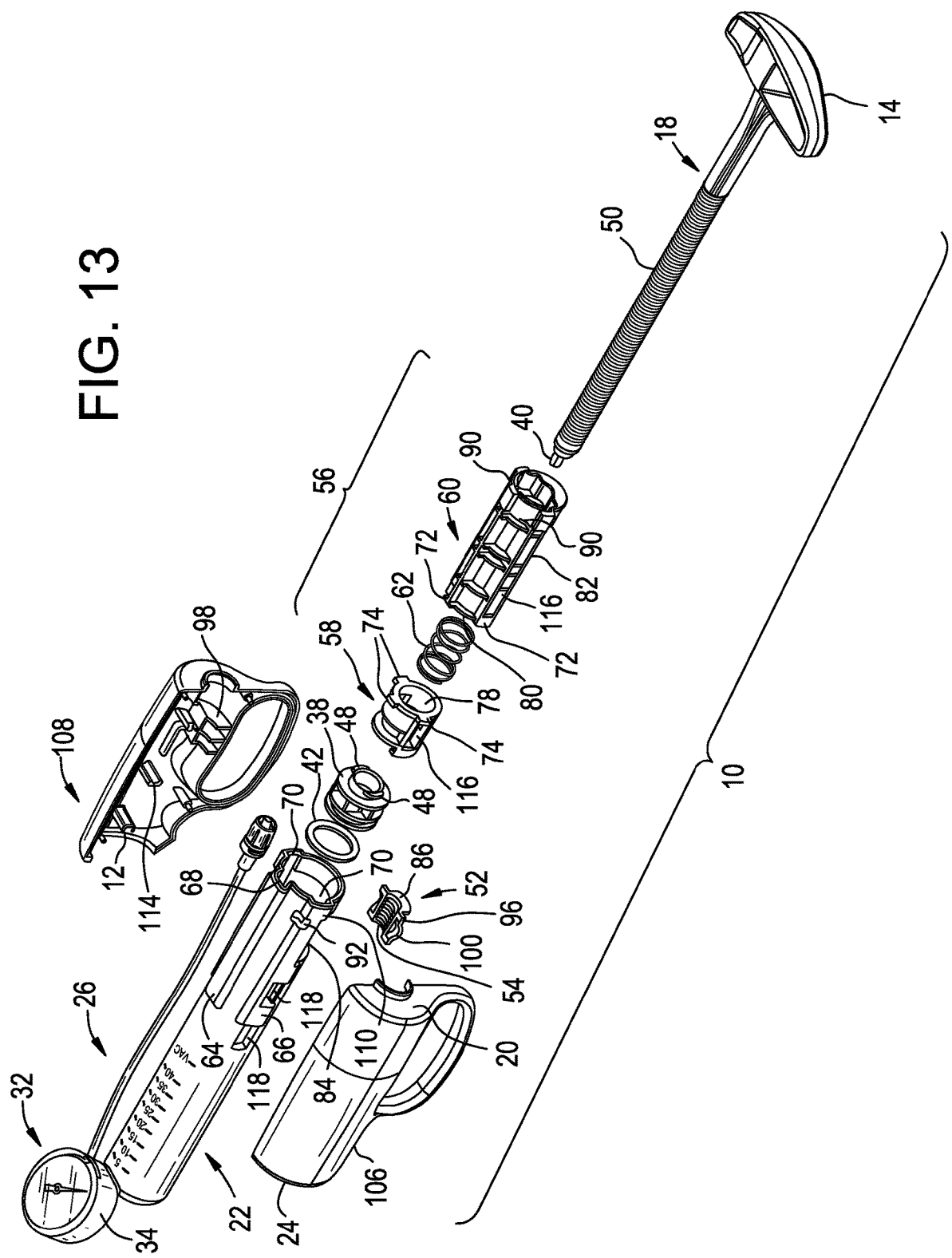
FIG. 13 is an exploded perspective view of the device shown in FIG. 1.

As shown in FIGS. 1 and 13, the user grip assembly 16 may be provided in two halves, 106 and 108, which snap or otherwise bond or secure together around the back portion 110 of the syringe body 22.

Each half 106, 108 of the user grip assembly 16 preferably has fingers 112, 114 which extend through notches 116 provided in the front carrier 58 and the rear carrier 60, to grasp the centralization spring 62 which is disposed between the two carriers 58, 60. Preferably, these notches 116 are sufficiently wide to allow compression of the centralization spring 62 by the fingers 112, 114 when the user grip assembly 16 is caused to transverse longitudinally forward or backward along the syringe body 22 during operation of the device 10. Preferably, the fingers 112, 114 are positioned close enough together to serve as stops against which the centralization spring 62 can contact in order to limit the longitudinal travel of the user grip assembly 16. Preferably, windows 118 are provided on each side of the syringe body 22 to coincide with the notches 116 in the carriers 58, 60 when the carrier assembly 56 is locked in place. These windows 118 allow the fingers 112, 114 to extend through and engage the centralization spring 62. When the front carrier 58 and the rear carrier 60 are assembled, the distance between the spring pocket 78 provided on the front carrier 58 and the spring pocket 80 provided on the rear carrier 60 is the same as the internal spacing between the fingers 112, 114 which project from the interior wall of the user grip assembly halves 106, 108.

Function of the device 10 will now be described. As shown in FIG. 1, the user grip assembly 16 provides the device 10 with a handle loop 12 which serves to guide the user's hand into the optimum control position for maximum comfort during operation. During operation, when a user grasps the device 10 by both the user grip assembly 16 surrounding the syringe body 22 and the handle 14 of the plunger 18, any longitudinal force applied to the plunger 18 first causes the user grip assembly 16 to move longitudinally for a set distance along the central, longitudinal axis of the syringe body 22. This initial movement is controlled by the centralization spring 62 as viewed in FIG. 2, contained between the front carrier 58 and the rear carrier 60 of the carrier assembly 56 which is locked within the syringe body 22, and finger pairs 112, 114 provided on the interior of user grip assembly halves 106, 108. The centralization spring 62 is configured to exert less force to resist any longitudinal movement of the user grip assembly 16 than the combined frictional resistance of the piston seal 42 and flow resistance of fluid passing through the fluid delivery passageway such as hose assembly 26.

Figure 5:
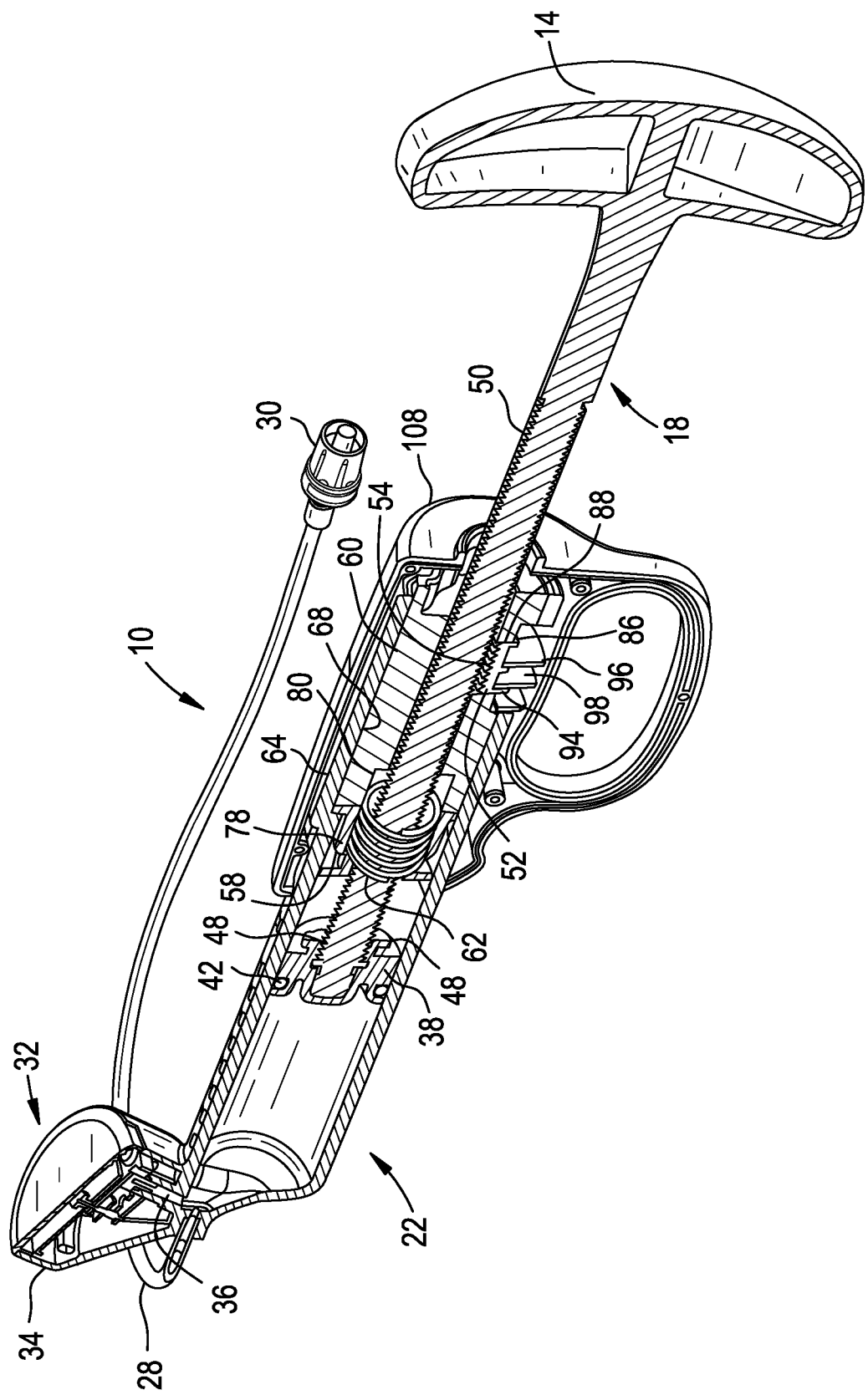
FIG. 5 is a cross-sectional view much like FIG. 2, but showing the device during filling.
Figure 7:
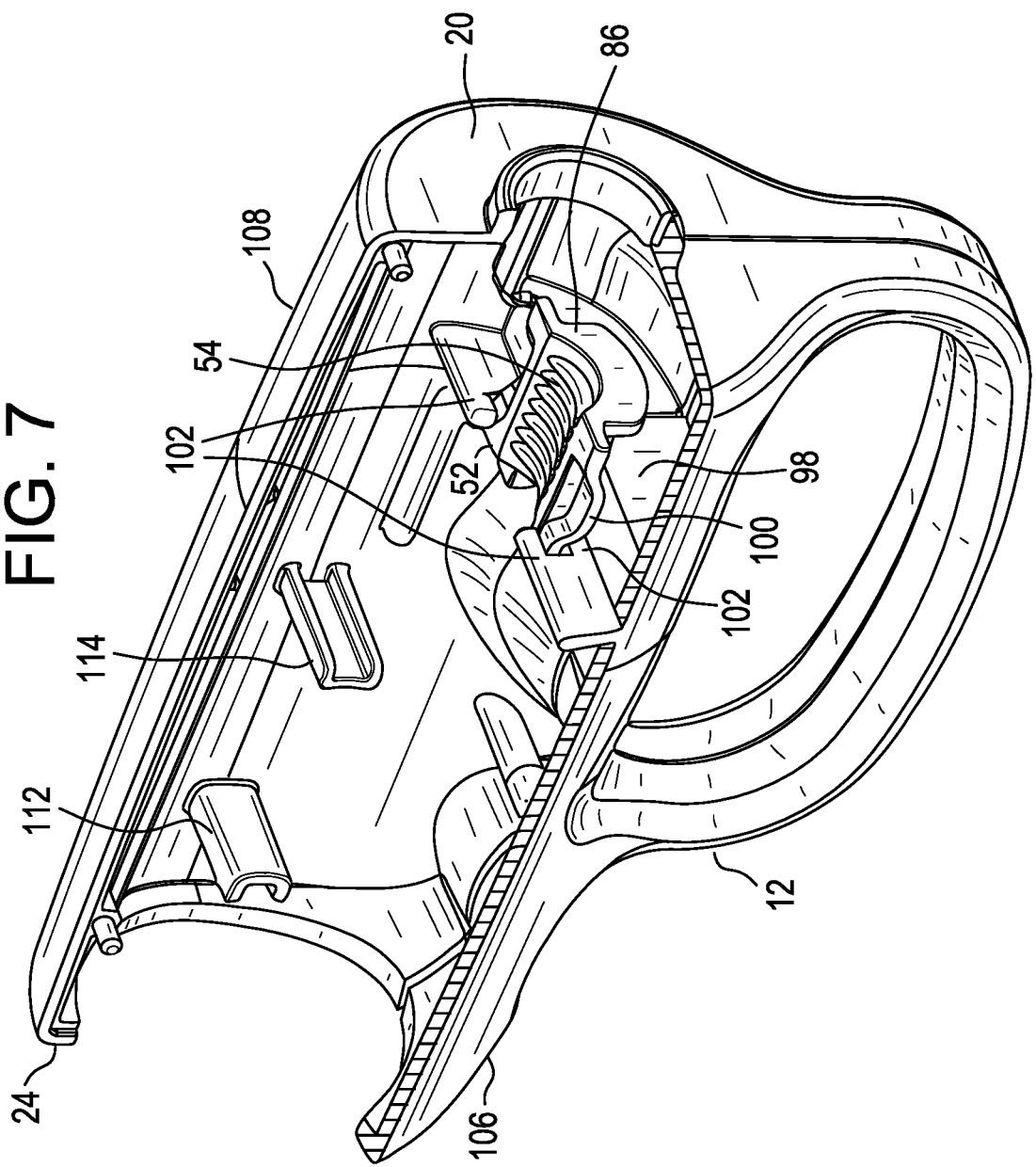
FIG. 7 is a sectional view much like FIG. 4, but showing the position of the half-nut during filing.

If during use, for example, a balloon catheter mounted to the Luer connecter 30 at the end of the hose 28 was taken to a desired pressure (as indicated on the pressure gauge 32), a subsequent deflation of that balloon could be initiated by simply pulling the handle 14 of the plunger 18 longitudinally away from the user grip assembly 16. This action causes the half-nut 52 contained within the user grip assembly 16 to withdraw from engagement with the thread 50 on the plunger 18 as shown in FIG. 5, through the interaction of cams 100 on the half-nut 52 with the cam followers 102 provided on the interior of the user grip assembly halves 106, 108, as shown in FIG. 7.

Figure 6:
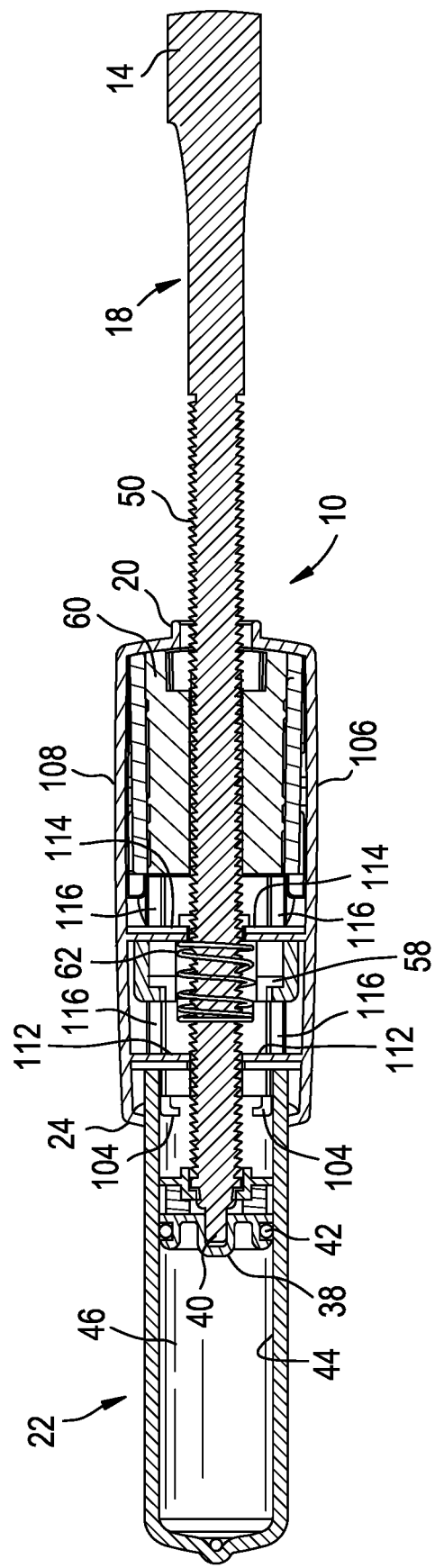
FIG. 6 is a cross-sectional view much like FIG. 3, but showing the device during filing.
Figure 8:
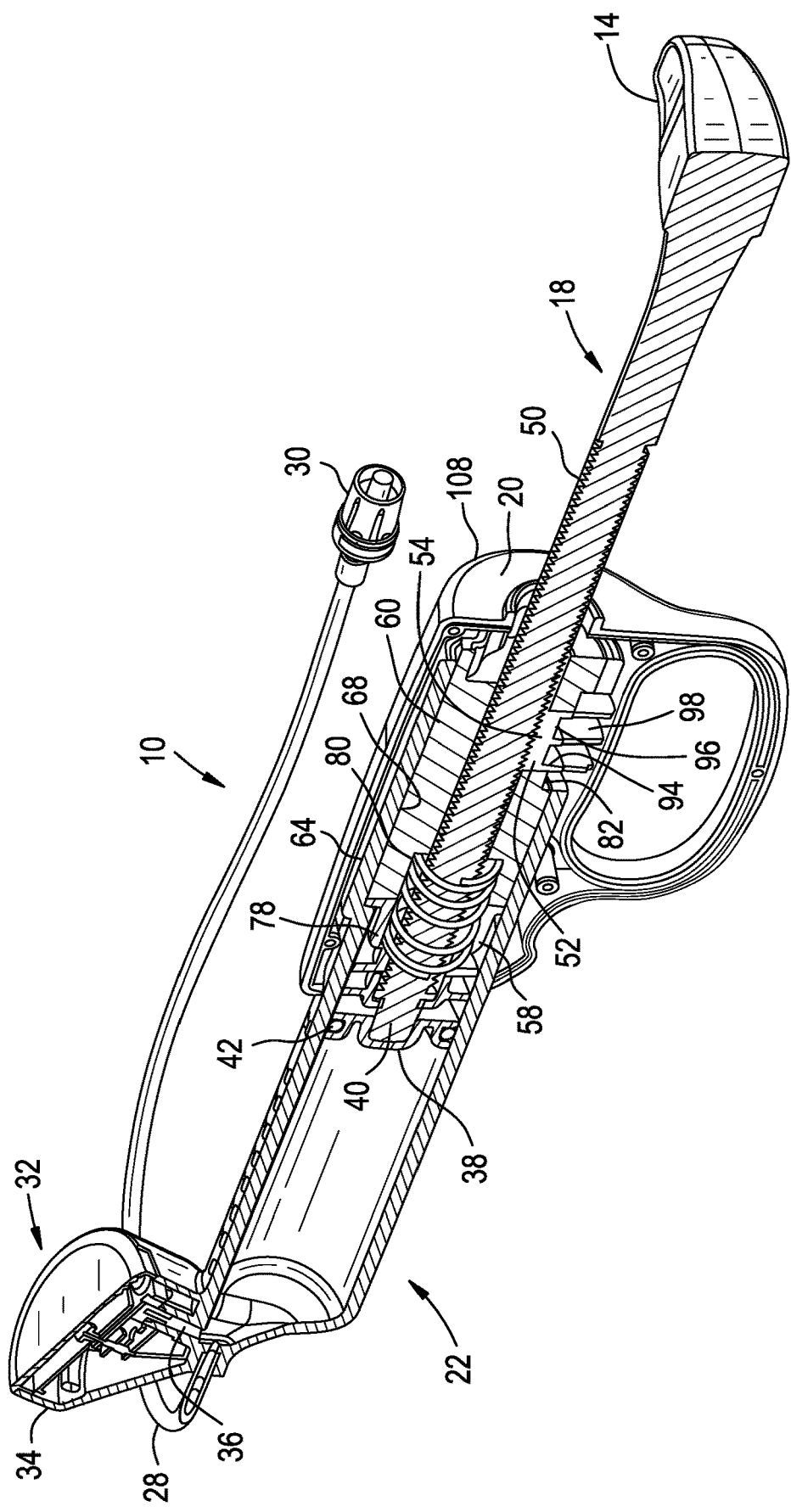
FIG. 8 is a cross-sectional view much like FIGS. 2 and 5, but showing the device in full vacuum mode.
Figure 9:
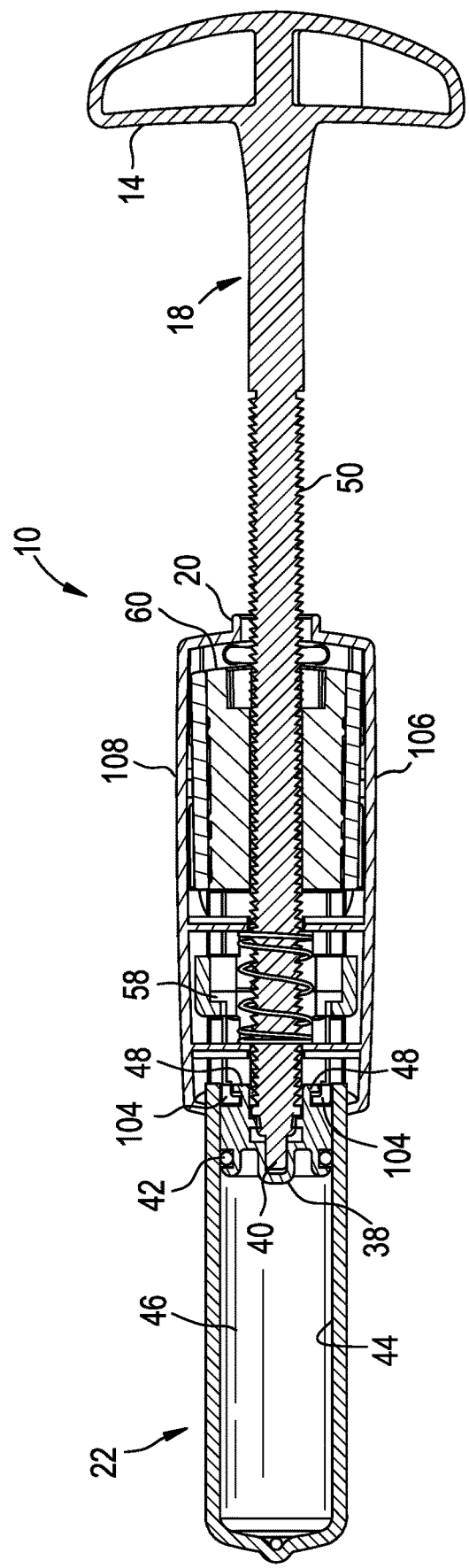
FIG. 9 is a cross-sectional view much like FIGS. 3 and 6, but showing the device in full vacuum mode.

Retraction of the half-nut 52 in this manner allows the plunger 18 to continue rearward in order to create a vacuum within the syringe body 22 to draw fluid from the attached catheter balloon and back into the syringe body 22. When held in this position, the centralization spring 62 is compressed by both rear fingers 114 against the spring pocket 78 of the front carrier 58, as shown in FIGS. 5 and 6, until user force between user grip assembly 16 and the handle 14 of the plunger 18 has been relaxed to allow the centralization spring 62 to expand and push the user grip assembly 16 back to its neutral position (i.e., relative to the syringe body 22). In the event that the plunger 18 has been fully withdrawn into its maximum rearward travel, means to retain the plunger 18 in a full vacuum position is available through a simple quarter turn of the plunger 18 to engage the detent ears 48 of the piston 38 with the mating detent receptacles 104 provided on the front carrier 58 of the carrier assembly 56, as shown in FIGS. 8 and 9.

Figure 4:
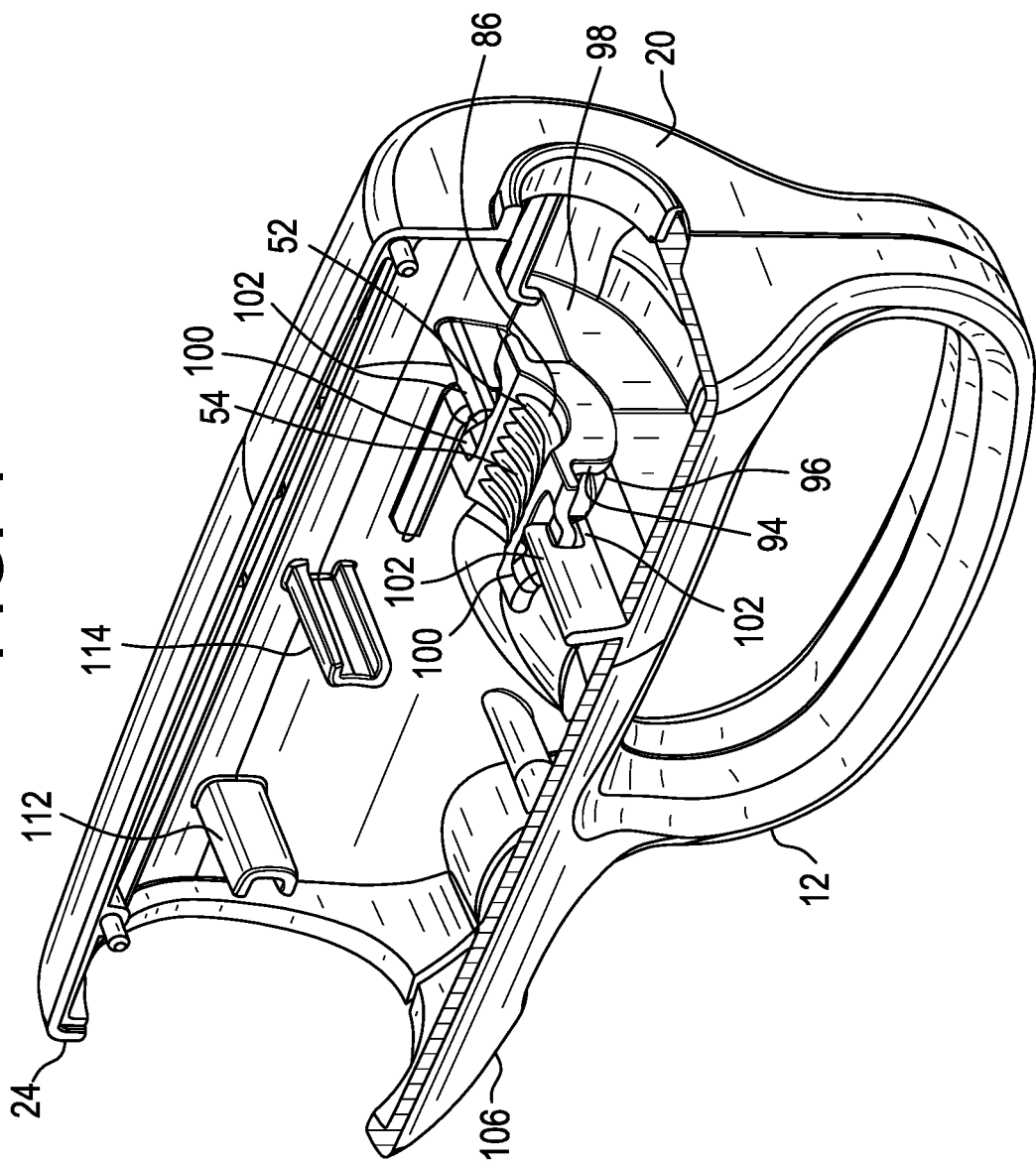
FIG. 4 is a sectional view of a user grip assembly of the device, showing a position of a half-nut component disposed therein during pressurizing of the device.
Figure 10:
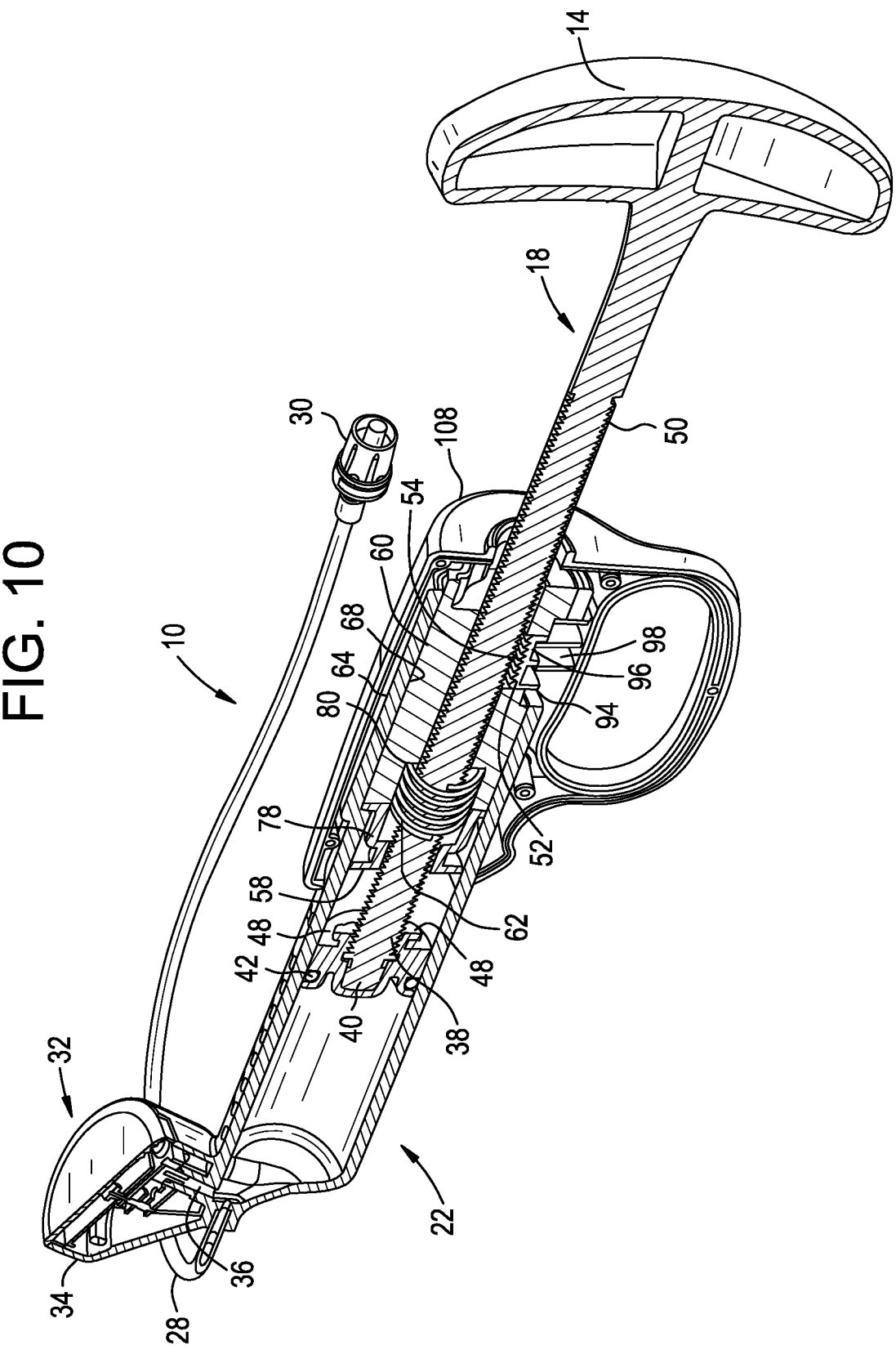
FIG. 10 is a cross-sectional view much like FIGS. 2, 5 and 8, but showing the device during dispensing.
Figure 11:
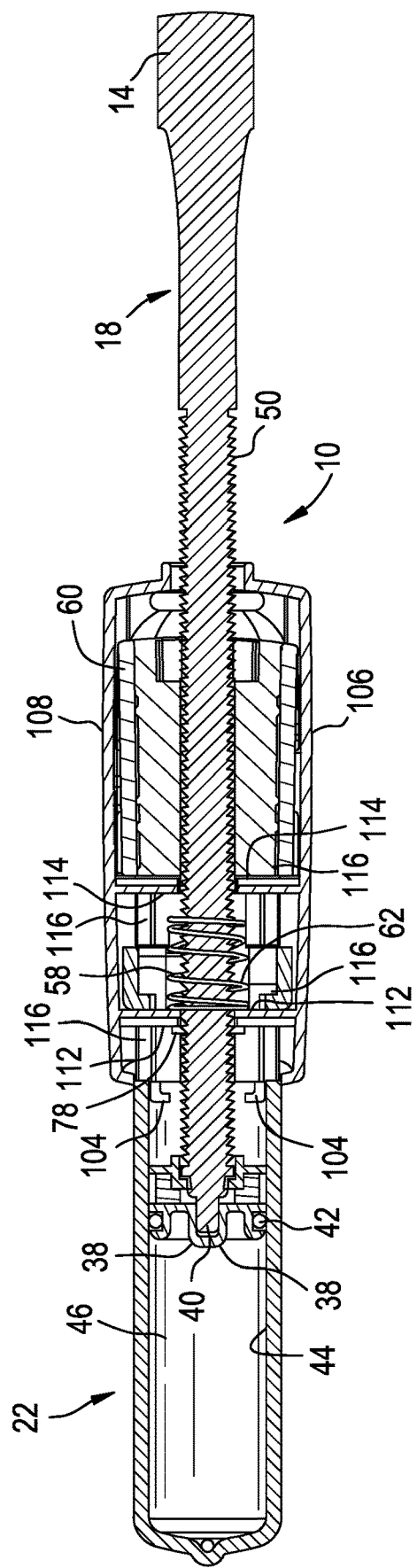
FIG. 11 is a cross-sectional view much like FIGS. 3, 6 and 9, but showing the device during dispensing.
Figure 12:
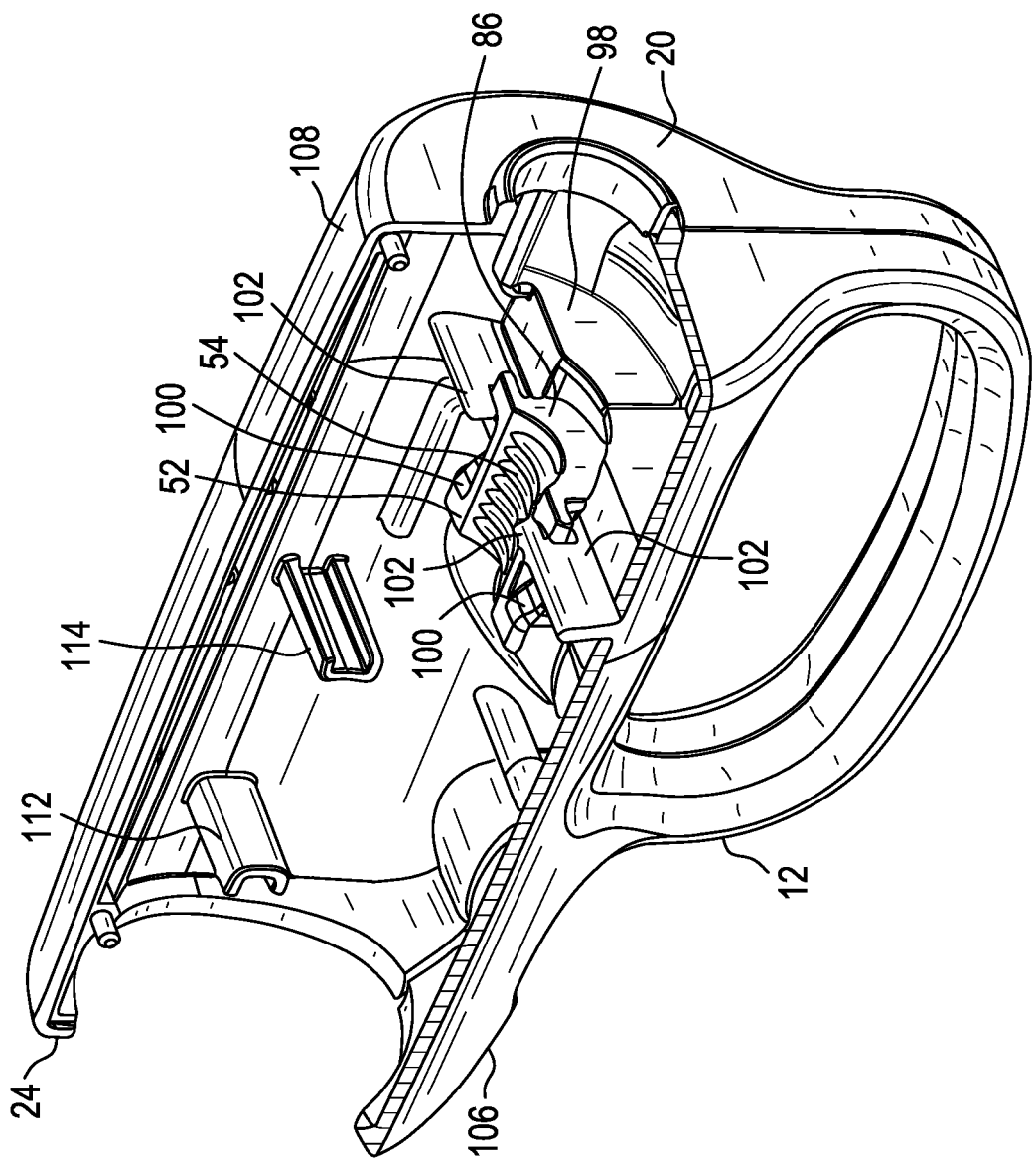
FIG. 12 is a sectional view much like FIG. 4, but showing the position of the half-nut component while the device is dispensing.

Conversely, should the user wish to dispense fluid from the syringe body 22, such as when rapidly filling a catheter balloon for it to approximate the size of the constriction being treated, moving the plunger 18 forward, toward the user grip assembly 16, causes the half-nut 52 to withdraw from the thread 50 on the plunger 18, as a result of interaction with the cams 100 on the half-nut 52 with the cam followers 102 which are provided on the interior of the user grip assembly halves 106, 108, as shown in FIGS. 11 and 12. In this mode (see also FIG. 10), both front fingers 112 compress the centralization spring 62 against the spring pocket 80 of the rear carrier 60. It should be noted that once the user-exerted forces to move the plunger 18 have been relaxed, the centralization spring 62 will restore the user grip assembly 16 to its neutral position, and its cam followers 102 will drive the half-nut 52 back into engagement with the thread 50 on the plunger 18 as user grip assembly 16 traverses back into its home position, as shown in FIGS. 2 and 4.

Referring to FIG. 13, the carrier assembly 56 is locked into place within the syringe body 22 by the latches 90 of the rear carrier 60 which engage latch slots 92 provided near the rear of the syringe body 22. Both the front carrier 58 and the rear carrier 60 are kept in proper orientation by their engagement with the top guide groove 68 and the side guide grooves 70 (which are provided by the top orientation channel 64 and the side orientation channels 66, respectively). The centralization spring 62 is contained in the spring pockets 78, 80 on the front carrier 58 and the rear carrier 60.

The half-nut 52 operates within the aperture 84 of the syringe body 22 and the half-nut pocket 82 of the rear carrier 60. While the engagement and disengagement motions of the half-nut 52 are controlled by the interaction of the cams 100 with the cam followers 102, the rearward thrust from the half-nut 52 while under load is transferred from the thrust surface 86 on the half-nut 52 to the thrust face 88 which is located in the half-nut pocket 82 of the rear carrier 60. The rear carrier 60, in turn, delivers the thrust it receives from the half-nut 52 to the syringe body 22 by means of the latches 90 on the rear carrier 60 which are positioned to transfer thrust to the latch slots 92, and therefore to the syringe body 22. Radial force upon the half-nut 52, while under load, is resisted by the three buttress elements 98 that are part of the user grip assembly halves 106, 108 and which are positioned directly below the three depending support ribs 94 which are formed on the bottom 96 of the half-nut 52. Whenever the half-nut 52 is positioned in its engaged position, the support ribs 94 bear upon the buttress elements 98 to resist radial movement of the half-nut 52 and maintain its parallel alignment with the thread 50 of the plunger 18 while under load. When the user grip assembly 16 moves longitudinally along the axis 76 of the syringe body 22, in response to force between the user grip assembly 16 and the plunger 18, the buttress elements 98 move from below the support ribs 94 on the half-nut 52 thereby allowing the cams 100 and the cam followers 102 to withdraw the half-nut 52 from the thread 50 on the plunger 18. Conversely, once the centralization spring 62 is allowed to restore the user grip assembly 16 to its neutral position, the half-nut 52 is driven back into engagement with the thread 50 of the plunger 18 through the interaction of the cams 100 with the cam followers 102 and the buttress elements 98 return to a position directly below the support ribs 94 on the half-nut 52.

Unlike prior art devices, the device 10 disclosed herein does not require that a user move a lever, push a button, etc., in order to change the use mode of the device. Therefore, when using the device, the user's hands are always positioned at the correct location required to proceed with the next action the user wishes to perform using the device.

In use, a user merely withdraws the plunger 18 in order to fill the device 10 with fluid, and presses the plunger 18 forward in order to purge the device 10 of unwanted air or fluid. When the device 10 is filled with fluid, the plunger 18 can either be rapidly advanced forward to allow quick balloon filling, or the user can just begin rotating the plunger handle 14 (such as in a clockwise direction) in order to create high balloon pressures by utilizing the mechanical advantage through engagement of the thread 50 on the plunger 18 with the thread 54 on the half-nut 52. Alternatively, the plunger 18 can either be rapidly pulled back to allow quick deflation of the balloon, or the user can just begin rotating the handle 14 of the plunger 18 (such as in a counter-clockwise direction) in order to slowly reduce the fluid pressure in the balloon. In other words, to execute micro movement of the plunger 18, a user need only rotate the handle 14; to execute macro movement of the plunger, a user need only push or pull the handle 14. This simplicity in use is possible because a half-nut 52 (or other suitable structure within the device 10) remains engaged with the plunger 18, except when the plunger 18 is being pushed or pulled by the user. All user motions are simple and intuitive, involving only pulling, pushing or rotating the handle 14 of the plunger 18.

In addition to the functional features described herein, the device 10 disclosed herein is configured such that it is easy to assemble. Assembly commences with installing the piston seal 42 onto the piston 38, and then sliding the piston 38 (with the piston seal 42 thereon) into the open end of the syringe body 22. The alignment tabs 74 on the front carrier 58 are then aligned with the guide grooves 68, 70 provided at the open end of the syringe body 22, and are allowed to drop into place. The centralization spring 62 is then placed into the spring pocket 78 on the front carrier 58. Next, the bosses 72 on the rear carrier 60 are aligned with the guide grooves 68, 70 to allow the rear carrier 60 to be inserted into the open end of the syringe body 22. The rear carrier 60 is then pressed into place behind the front carrier 58, which allows the latches 90 on the rear carrier 60 to engage the corresponding latch slots 92 on the syringe body 22, and trap the centralization spring 62 within the spring pockets 78, 80 of the two carriers 58, 60. The plunger 18 is then inserted through the rear carrier 60, until the end 20 of the plunger 18 contacts and snaps into the piston 38 such that the piston 38 becomes retained on the end 20 of the plunger 18. The half-nut 52 is then inserted through the aperture 84 in the syringe body 22 and into position within the half-nut pocket 82 on the rear carrier 60. Finally, the two halves 106, 108 of the user grip assembly 16 are aligned with each other, engaged with the cams 100 of the half-nut 52 via the cam followers 102, and engaged with the centralization spring 62 via the fingers 112, 114. The two halves 106, 108 are then secured together after which time the device 100 is ready for use.

FIGS. 14-32 relate to a fluid displacement and pressurizing device 10A which is in accordance with a second, more preferred embodiment of the present invention. The device 10A shown in FIGS. 14-32 is much like the device 10 shown in FIGS. 1-13, except for some differences directed to improve the overall structure and function. The device 10A will be described using like numbers to identify like parts. At times, description will be omitted with the understanding that the like numbered parts and their operation is much like that of the previously described device 10, but the differences (where they exist) between the two devices 10 and 10A will be explained in detail.

Figure 14:
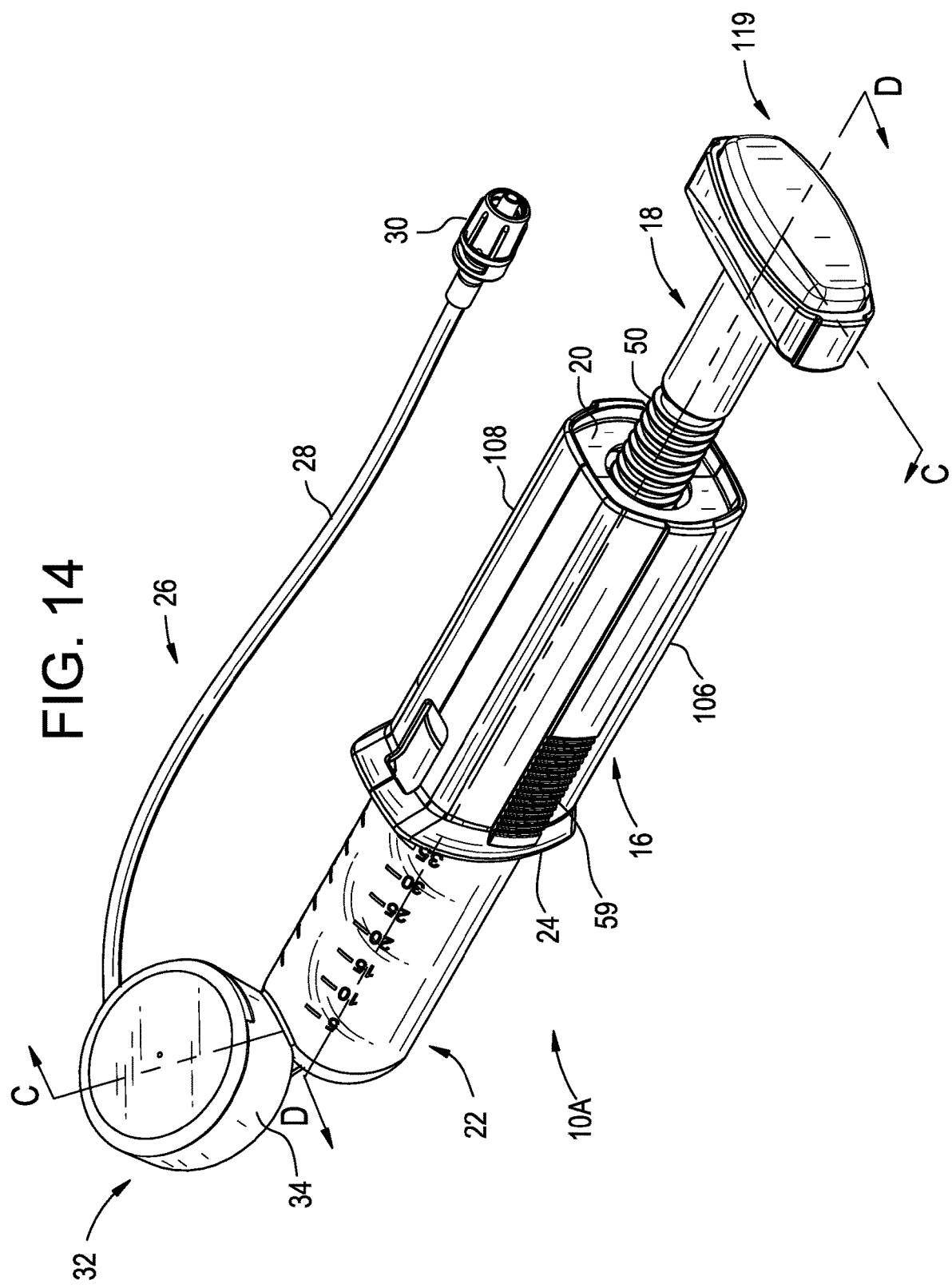
FIG. 14 is a perspective view of a fluid displacement and pressurizing device which is in accordance with a second, more preferred embodiment of the present invention.

As shown in FIG. 14, much like the device 10 shown in FIG. 1, the device 10A comprises a user grip assembly 16. A plunger 18 extends from one end 20 of the user grip assembly 16, and a syringe body 22 extends from the other end 24. The syringe body 22 is configured to be engaged with a hose assembly 26 or the like, which may include a hose 28 and a Luer connector 30 at the end of the hose 28, ultimately for connection to a device such as a catheterization balloon to be pressurized, etc. by the device 10A. A pressure gauge 32 is preferably provided, for indicating the fluid pressure inside the device 10A. The pressure gauge 32 may be retained in an integral housing 34 which is part of the syringe body 22. Alternatively, the pressure gauge 32 may extend from the syringe body 22, threaded into a threaded bore provided on the syringe body 22. The plunger 18 includes a handle 14 for engagement by a user, and preferably instead of providing a loop 12 such as is shown in FIG. 1, the device 10A shown in FIG. 14 includes hand engagement surfaces 59 on the sides of the user grip assembly 16. The plunger 18 has a thread 50 thereon, and the user grip assembly 16 may be provided in two halves, 106 and 108, which snap or otherwise bond or secure together around a back portion of the syringe body 22. One major difference between the device 10 and the device 10A is preferably the handle 14 of the plunger 18 of the device 10A has a vacuum release button 119 disposed thereon. This will be described in more detail later herein.

The user grip assembly 16 provides the hand engagement surfaces 59 (or other type of grip structure) for engagement by a user using one hand, and the user can push, pull or twist the handle 14 of the plunger 18, as well as push the vacuum release button 119, using the other hand.

The device 10A is configured such that a user merely pulls on the handle 14 of the plunger 18 in order to fill the device 10A with fluid, and presses the handle 14 of the plunger 18 forward in order to purge the device 10A of unwanted air or fluid. When the device 10A is filled with fluid, the user can rapidly push the handle 14 of the plunger 18 forward to fill the balloon (for example) quickly, or the user can just begin rotating the handle 14 of the plunger 18 (such as in a clockwise direction) in order to slowly add pressure to the balloon. Alternatively, the user can pull the handle 14 of the plunger 18 back rapidly to quickly deflate the balloon, or the user can just begin rotating the handle 14 of the plunger 18 (such as in a counter-clockwise direction) in order to slowly reduce the fluid pressure in the balloon. Furthermore, the user can press the vacuum release button 119 to release the vacuum in the device 10A.

In other words, to execute micro movement of the plunger 18, a user need only rotate the handle 14 of the plunger 18; to execute macro movement of the plunger 18, a user need only push or pull the handle 14 of the plunger 18; and to quickly release the vacuum in the device 10A, a user need only press the vacuum release button 119. All user motions are simple and intuitive.

Figure 15:
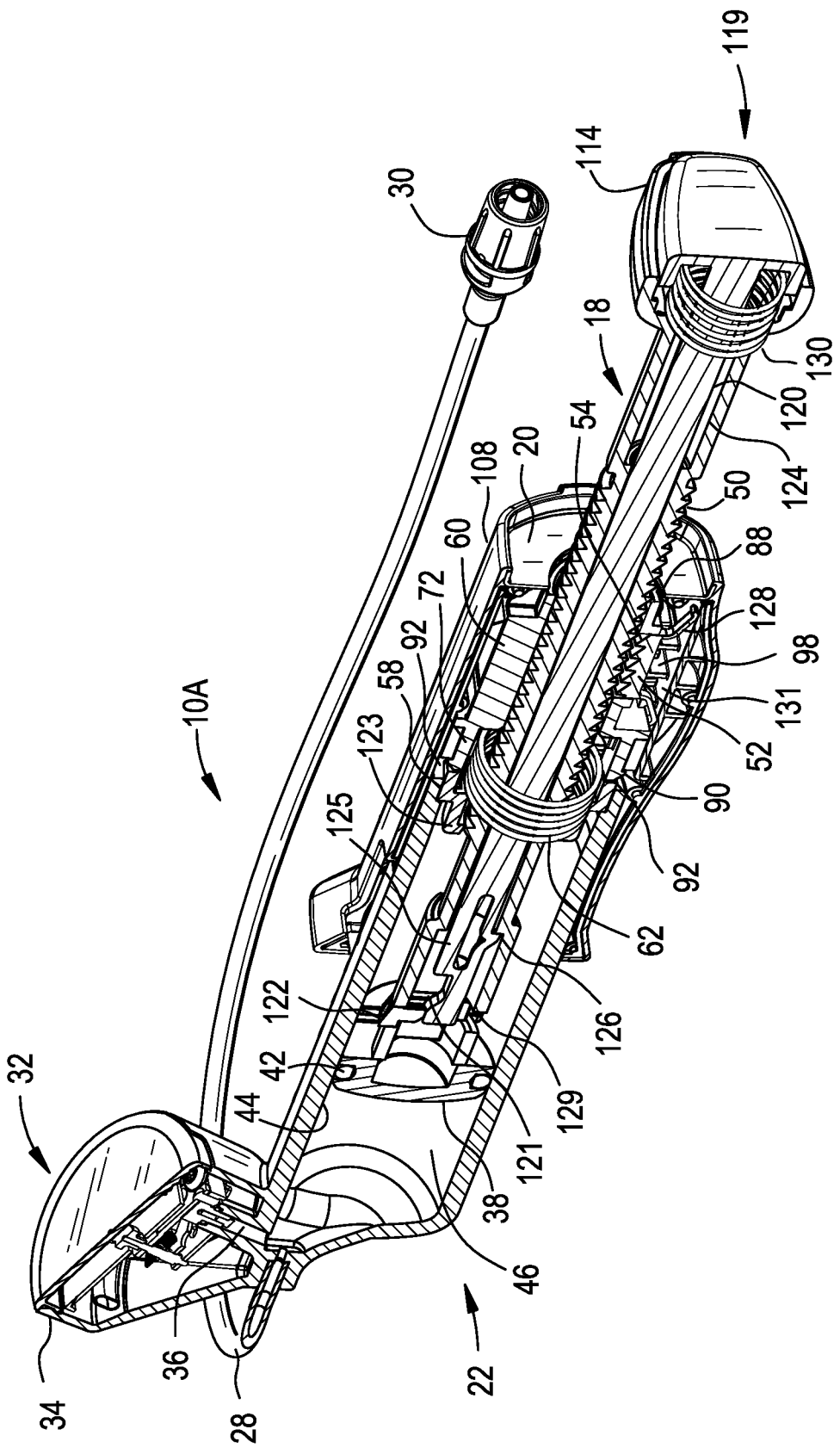
FIG. 15 is a cross-sectional view of the fluid displacement and pressurizing device shown in FIG. 14, taken along line C-C of FIG. 14, showing the device during filling of the device (i.e., the device in "fill mode")
Figure 16:
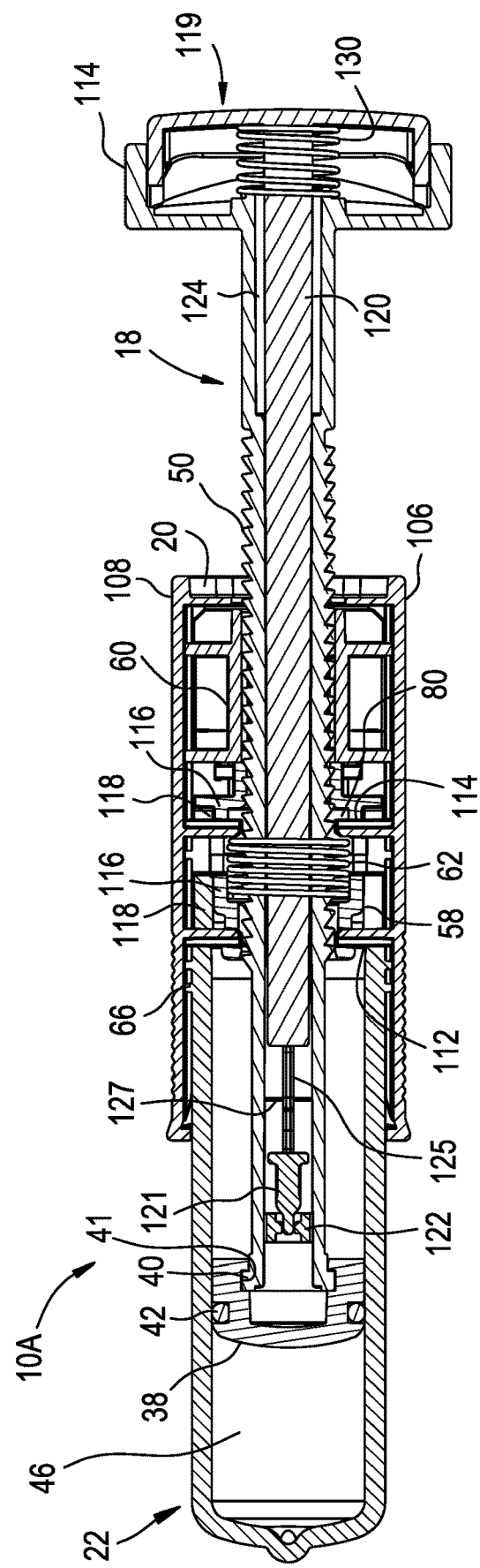
FIG. 16 is a cross-sectional view of the fluid displacement and pressurizing device shown in FIG. 14, taken along line D-D of FIG. 14, showing the device in fill mode.

FIGS. 15 and 16 provide cross-sectional views in which the internal components of the device 10A can be seen. Specifically, FIG. 15 is a cross-sectional view of the device 10A taken along line C-C of FIG. 14, while FIG. 16 is a cross-sectional view of the device 10A taken along line D-D of FIG. 14.

As shown in FIGS. 15 and 16, a piston 38 is engaged with the end 40 of the plunger 18, and at least one piston seal 42 (such as one or more o-rings) is disposed on the piston 38. The piston seal 42 engages an internal wall 44 of the syringe body 22 such that a pressure chamber 46 therein can be pressurized, and fluid is not able to move from the pressure chamber 46, past the piston seal 42. As will be described, preferably the plunger 18 of the device 10A is hollow (i.e., has a longitudinal bore). As such, preferably the piston 38 is mounted on the end 40 of the plunger 18 via a simple "T" feature formed on the end 40 of plunger 18 which is configured to engage a corresponding receiving slot 41 on the proximal end of piston 38.

With regard to device 10 shown in FIGS. 1-13, the interaction of the detent ears 48 with detent receptacles 104 serves the purpose of retaining plunger 18 under vacuum conditions; however, user operation requires an intentional alignment of the detent ears 48 with the detent receptacles 104 through rotational manipulation of the plunger handle 14 into specific positions.

Unlike the device 10 shown in FIGS. 1-13, preferably the piston 38 of the device 10A does not include any detent ears 48. Instead, for more user convenience to allow engagement and release of a vacuum detent mechanism from any rotational position of plunger handle 14, the improved device 10A (shown in FIGS. 14-32) provides that the plunger 18 includes a notch 129 which aligns, supports and retains a deflectable retractable latch 122. The vacuum release button 119 preferably includes a shaft 120 which extends along a longitudinal bore provided in the plunger 18, and a distal end of the shaft 120 provides a deflectable beam element 125 which has a cam 121 thereon which interacts with the deflectable retractable latch 122. The vacuum release button 119 is preferably retained within the plunger 18 via a detent 126 on the shaft 120, which engages an internal shoulder 127 within the plunger 18. Preferably, a vacuum release return spring 130 is disposed between the vacuum release button 119 and a proximal end of the plunger 18.

In operation, the cam 121 retains the latch 122 in place, but the cam 121 withdraws down into the notch 129 of plunger 18 when the vacuum release button 119 is depressed into the handle 14, due to the shaft 120 shifting distally within the plunger 18. Preferably, a front carrier 58 is provided in the device 10A, and a distal end of the front carrier 58 includes a circular ledge 123. The retractable latch 122 remains extended above the surface of the plunger 18 until the vacuum release button 119 has been depressed or until the retractable latch 122 encounters the circular ledge 123 provided on the distal end of the front carrier 58. The ledge 123 is configured to receive the latch 122 regardless of its rotational position. Whenever the plunger 18 is withdrawn firmly to its maximum travel distally, as when creating a vacuum within the syringe body 22, the retractable latch 122 encounters the circular ledge 123. As they bypass one another, the circular ledge 123 pushes the retractable latch 122 into the notch 129 against the cam 121 which, in turn, is deflected. The retractable latch 122 is allowed this additional momentary movement by the deflectable beam element 125 which is provided at the end of the shaft 120 and which provides the cam 121. Once the plunger 18 has been withdrawn sufficiently to allow the latch 122 to clear the circular ledge 123 on the distal end of the front carrier 58, the beam element 125 recovers from its deflection and forces the cam 121 back toward its normal position which, in turn, drives the latch 122 out of notch 129 where it engages the distal edge of the circular ledge 123. Once in this position, the latch 122 holds the plunger 18 against the force of vacuum within syringe body 22 until the vacuum release button 119 is depressed into the handle 14 to drive the cam 121 distally and withdraw the latch 122 into the notch 129. This withdrawal of the latch 122 from behind the circular ledge 123 releases the plunger 18 from retention in the vacuum position.

Figure 32:
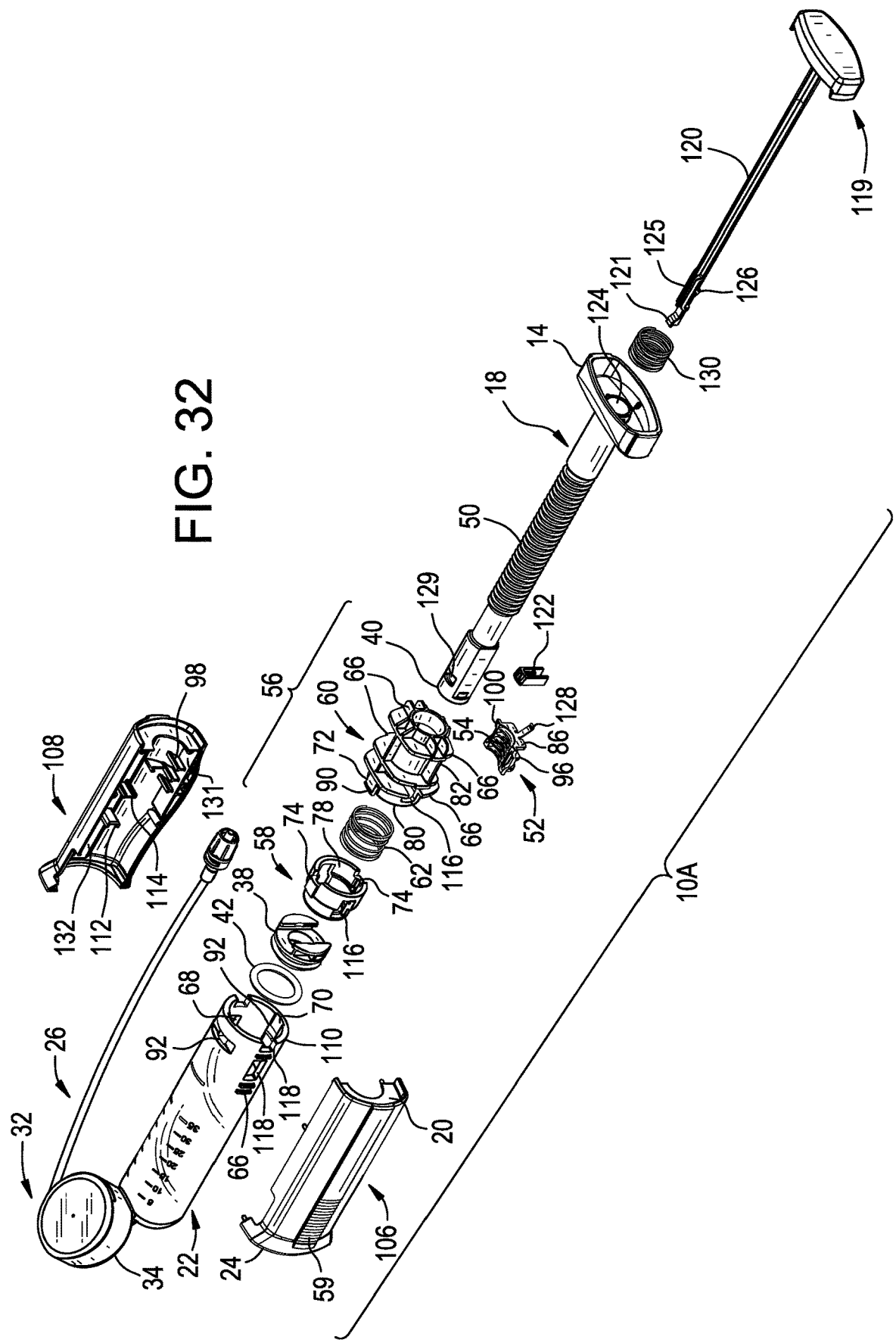
FIG. 32 is an exploded view of the device shown in FIG. 14.

As shown in FIG. 32, preferably the device 10A includes a single guide groove 70, as opposed to the pair of side guide groves 70 as are provided in the device 10 shown in FIG. 13. Additionally, preferably the device 10A employs side alignment features 66 instead of side orientation channels 66, as are provided in the device 10 shown in FIG. 13. These side alignment features 66 of the improved device 10A engage within channel ways 132 provided on the interior of the user grip assembly halves 106, 108 much the same as the original side orientation channels 66 of the device 10 shown in FIGS. 1-13.

The device 10A shown in FIGS. 14-32 also provides cam followers 102 which are different than the cam followers 102 of the device 10 shown in FIG. 1-13. Specifically, the cam followers 102 do not have a lower cam portion which is configured to move the half-nut 52 into engagement with the threads 50 on the plunger 18. Instead, the device 10A shown in FIGS. 14-32 replaces the function of the cam followers 102 through provision of a spring load force against upper cams 102 that is supplied by spring fingers 128 which are formed as integral elements of the half-nut 52. The spring fingers 128 are configured to traverse within a gap that is provided between buttress elements 98 in the device 10A, and is configured to bear against a spring support surface 131 which is provided on the user grip halves 106, 108, inside the device 10A. By eliminating any need for the cams 100 to be guided by lower cam followers 102, the spring fingers 128 on the half-nut 52 provide for more faithful following of the cams 100 upon the upper cam followers 102 and therefore assure more immediate and complete engagement of the threads 54 on the half-nut 52 with the threads 50 on the plunger 18 without the engagement losses previously imposed by operating clearances between the cam 100 and the cam followers 102.

The device 10A is configured to operate in several different modes. Specifically, FIGS. 15-17 relate to fill mode, FIGS. 18-20 relate to pressurizing mode, FIGS. 21-23 relate to dispense mode, FIGS. 24-25 relate to vacuum locked mode, and FIGS. 28-29 relate to vacuum release mode.

Figure 17:
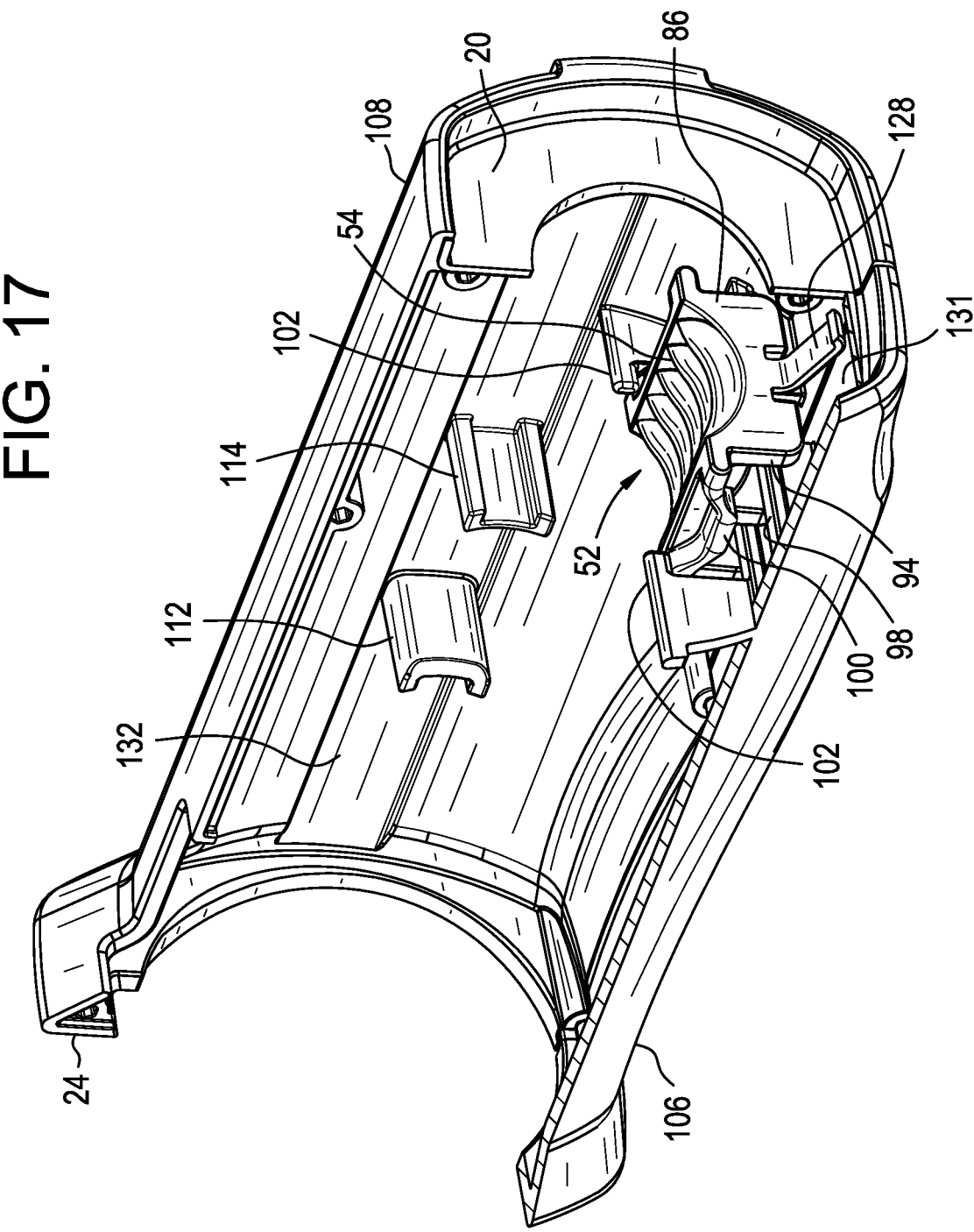
FIG. 17 is a sectional view of a user grip assembly of the device shown in FIGS. 14-16, showing a position of a half-nut component when the device is in fill mode.

Referring to FIGS. 15-17, during fill mode the half-nut 52 has moved back and down in the device 10A, out of engagement with the thread 50 on the plunger 18, during which time the plunger 18 is being pulled out relative to the user grip assembly 16.

Figure 18:
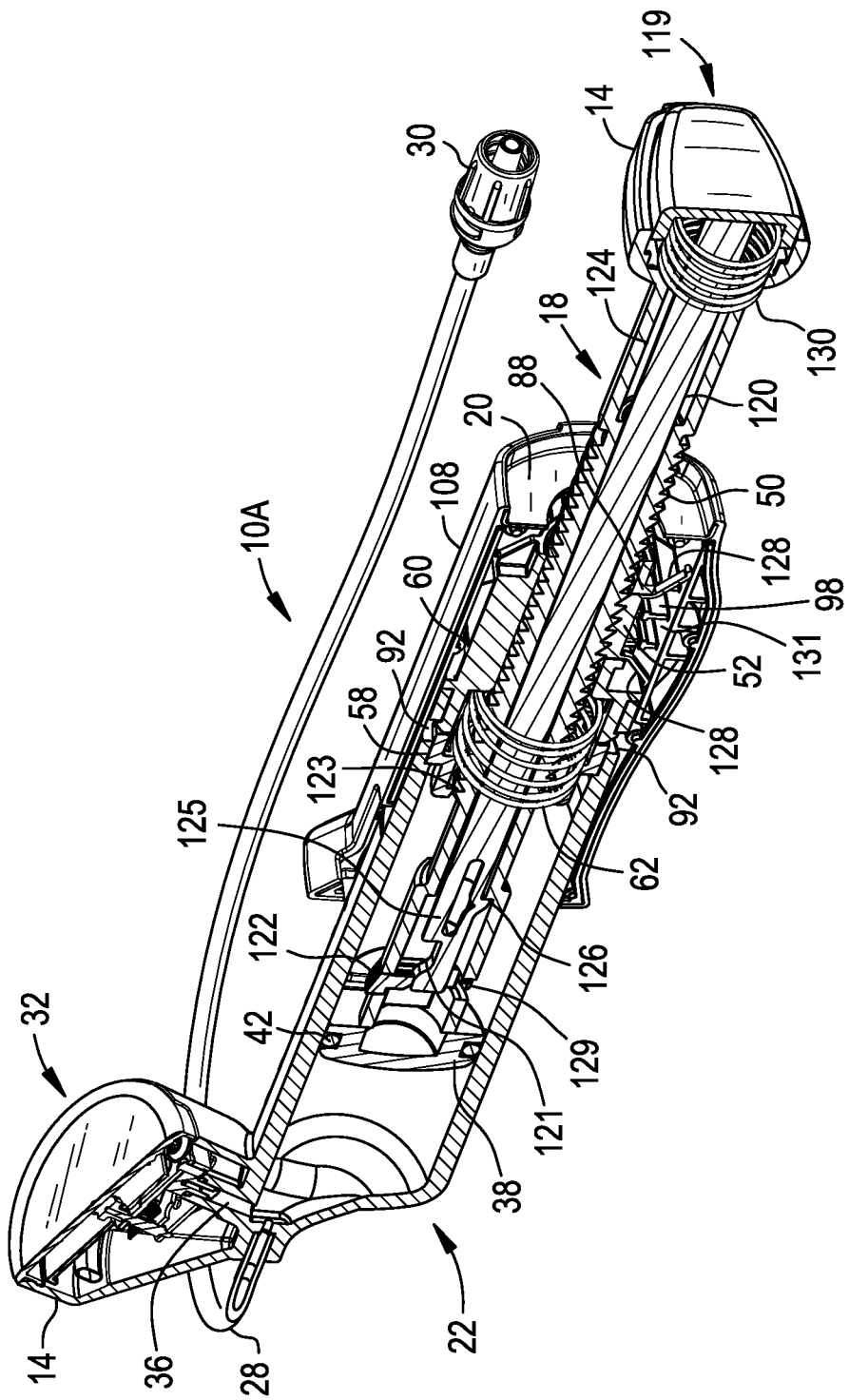
FIG. 18 is a cross-sectional view much like FIG. 15, but showing the device during pressurizing (i.e., the device in "pressurizing mode")
Figure 19:
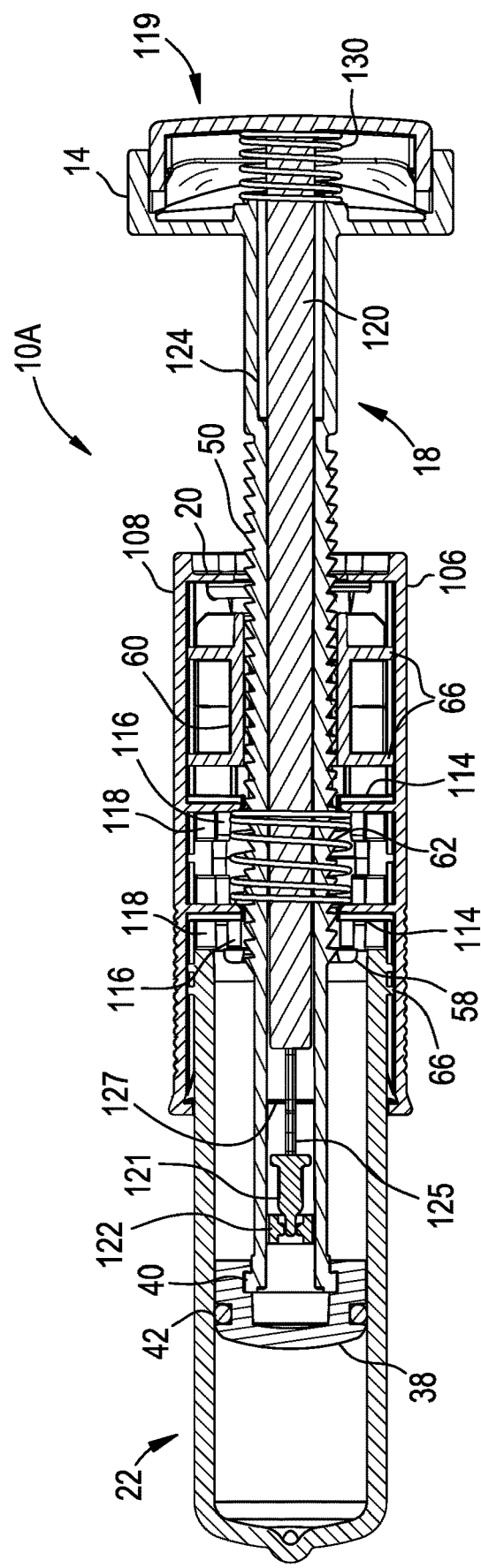
FIG. 19 is a cross-sectional view much like FIG. 16, but showing the device in pressurizing mode.
Figure 20:
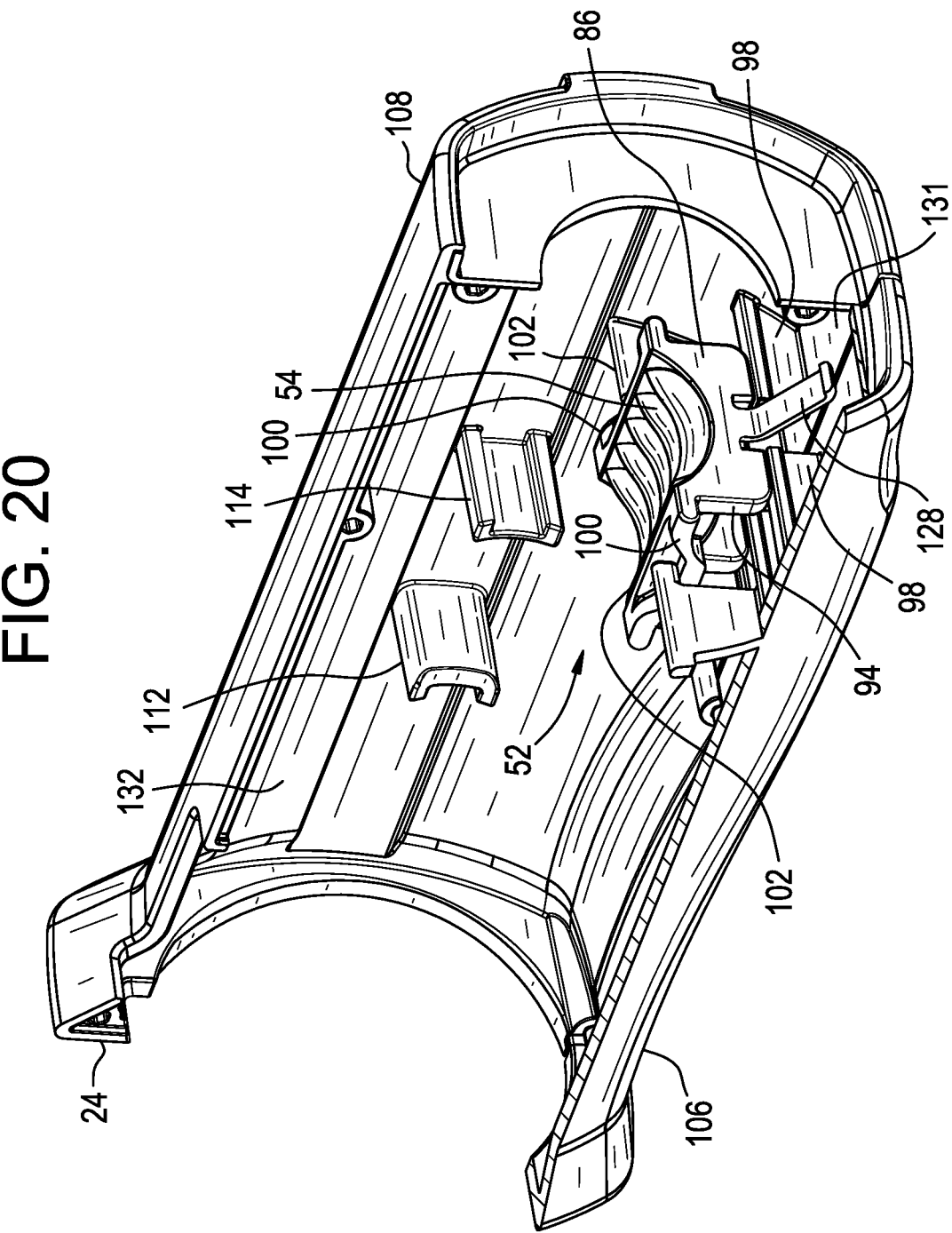
FIG. 20 is a sectional view of a user grip assembly of the device shown in FIG. 14, showing a position of a half-nut component disposed therein during pressurizing of the device.

Referring to FIGS. 18-20, during pressurizing mode the half-nut 52 is engaged with the thread 50 on the plunger 18, during which time the plunger 18 is being rotated relative to the user grip assembly 16.

Figure 21:
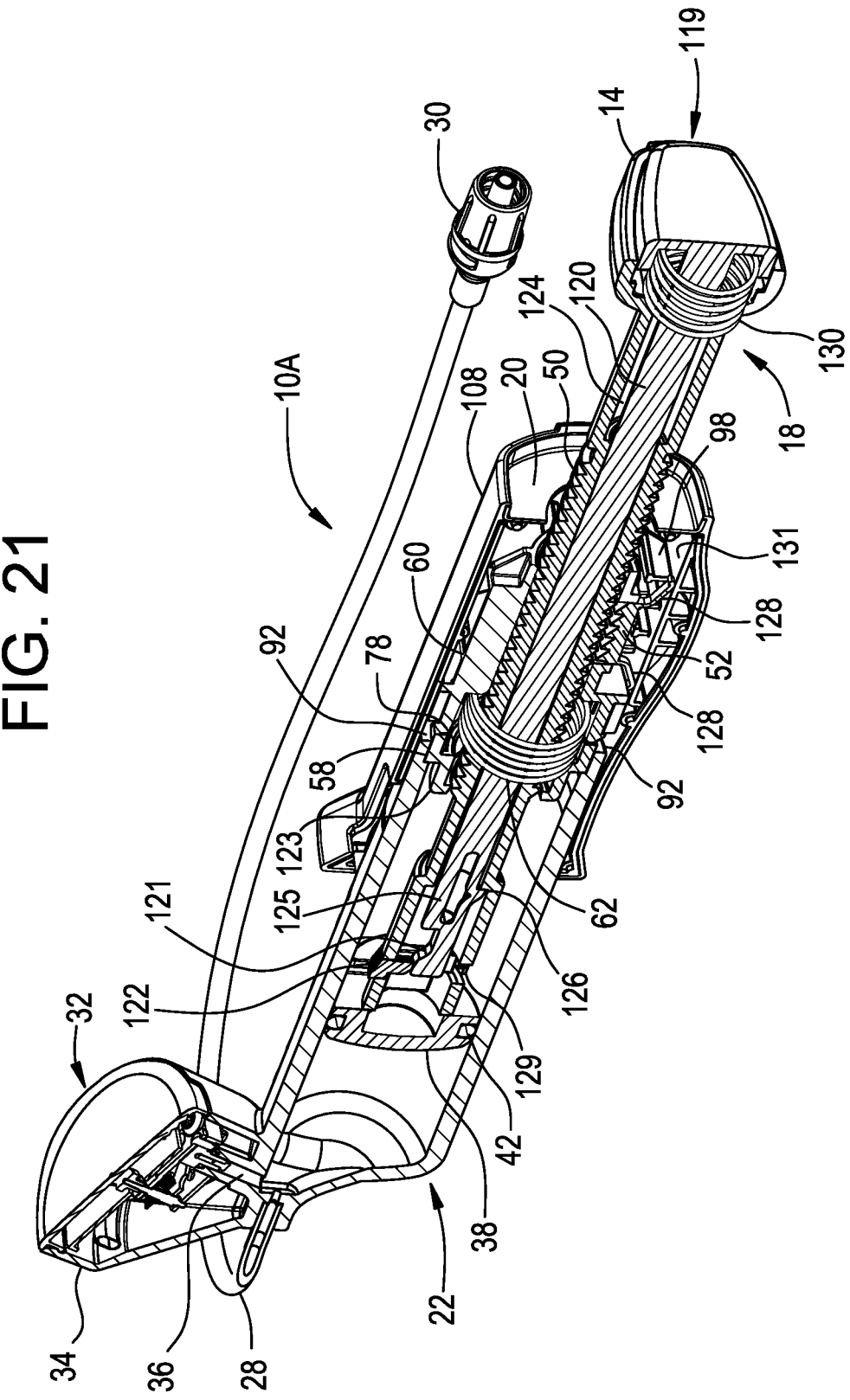
FIG. 21 is a cross-sectional view much like FIGS. 15 and 18, but showing the device while dispensing (i.e., the device in "dispense mode")
Figure 22:
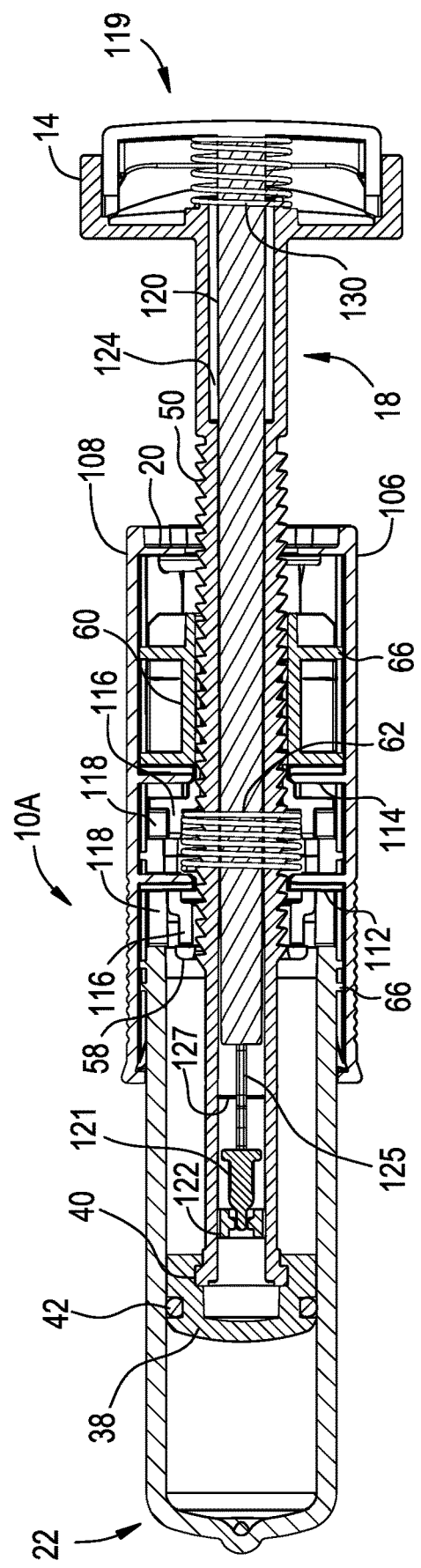
FIG. 22 is a cross-sectional view much like FIGS. 16 and 19, but showing the device in dispense mode.
Figure 23:
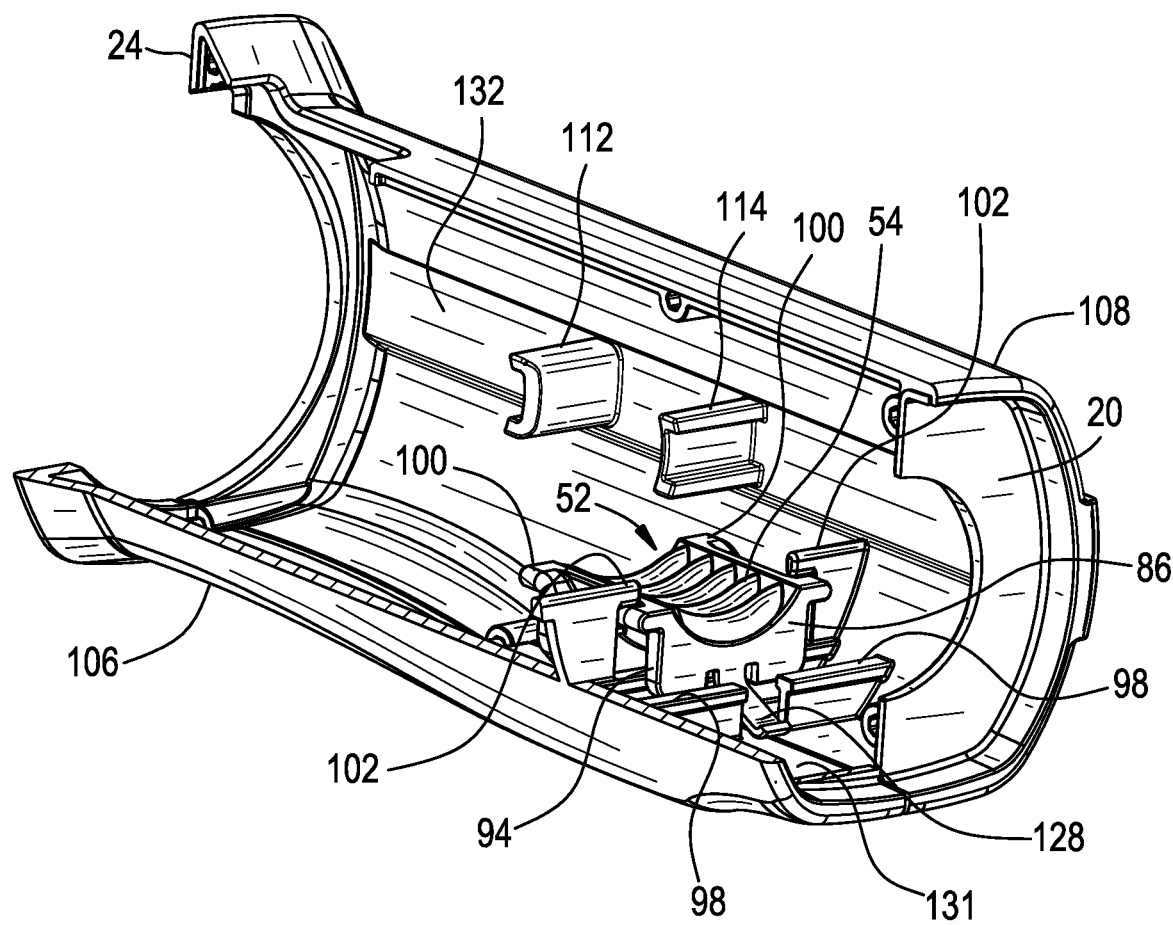
FIG. 23 is a sectional view much like FIG. 20, but showing the position of the half-nut component when the device is in dispense mode.

Referring to FIGS. 21-23, during dispense mode the half-nut has moved forward and down in the device 10A, out of engagement with the thread 50 on the plunger 18, during which time the plunger 18 is being pushed in relative to the user grip assembly 16.

Figure 24:
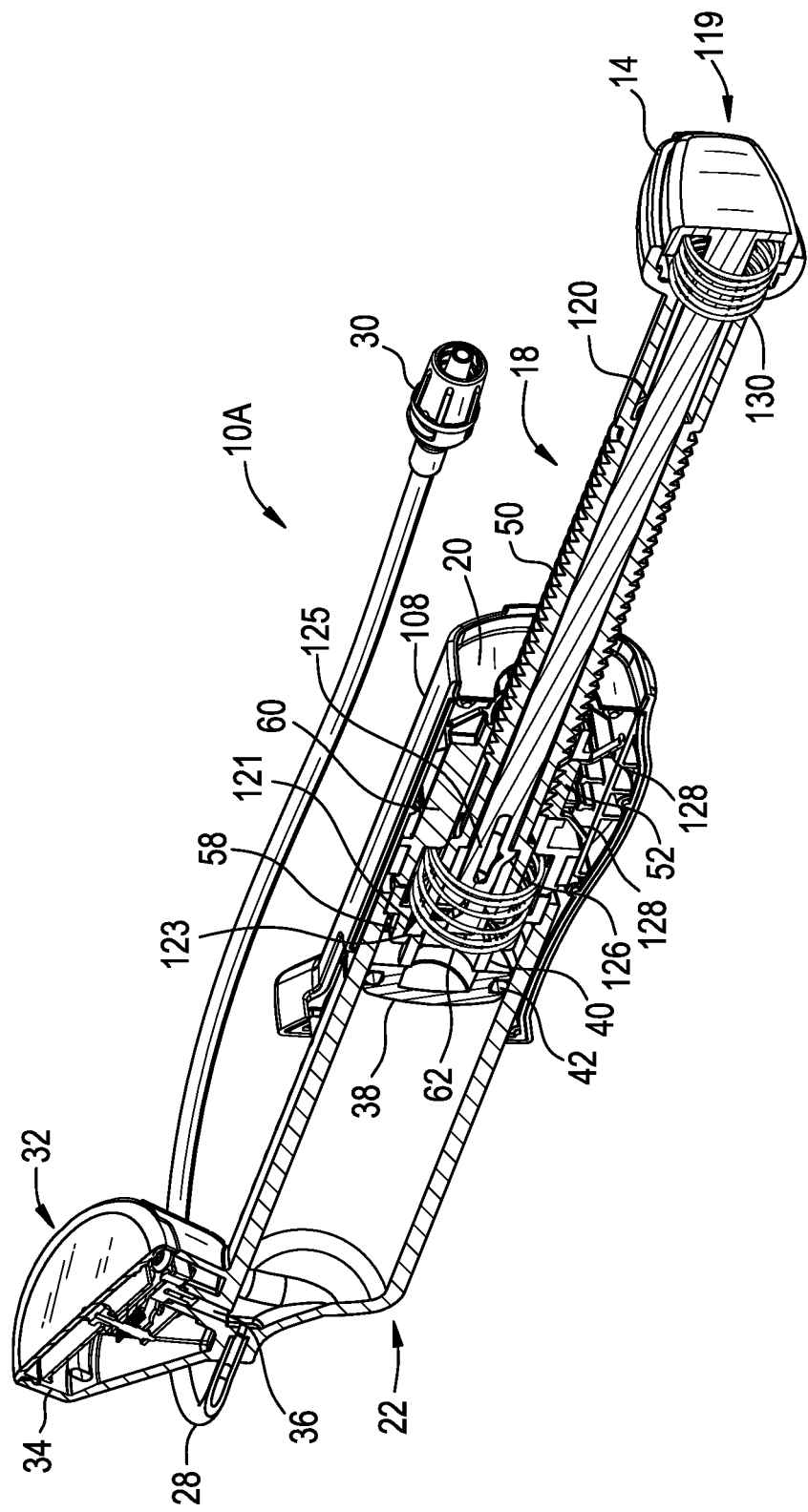
FIG. 24 is a cross-sectional view much like FIGS. 15, 18 and 21, but showing the device after the vacuum therein has been locked (i.e., the device in "vacuum locked mode")
Figure 25:
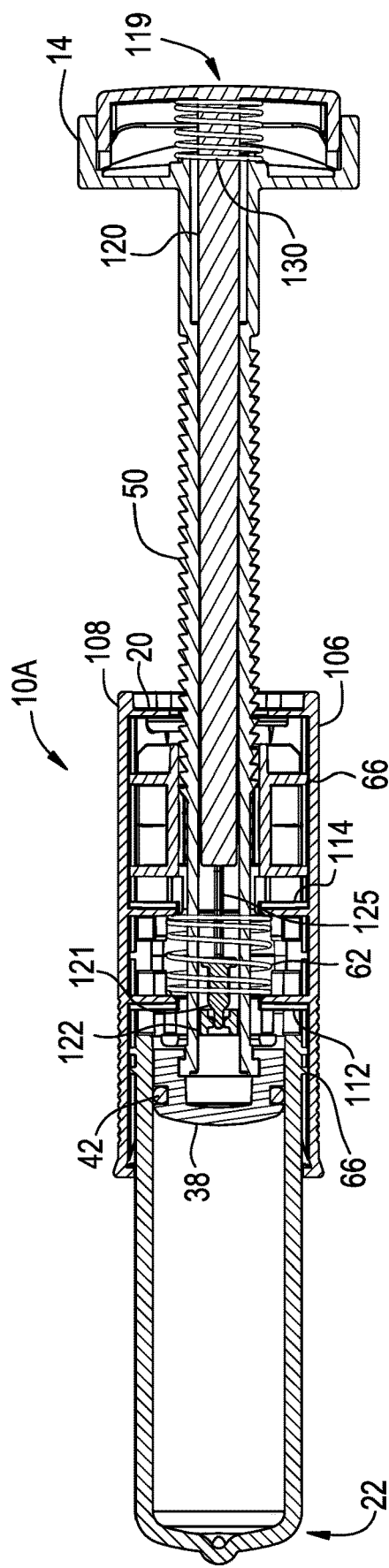
FIG. 25 is a cross-sectional view much like FIGS. 16, 19 and 22, but showing the device in vacuum locked mode.

Referring to FIGS. 24-25, during vacuum locked mode the plunger 18 has been pulled out of the user grip assembly 16 to its fullest extent.

Figure 28:
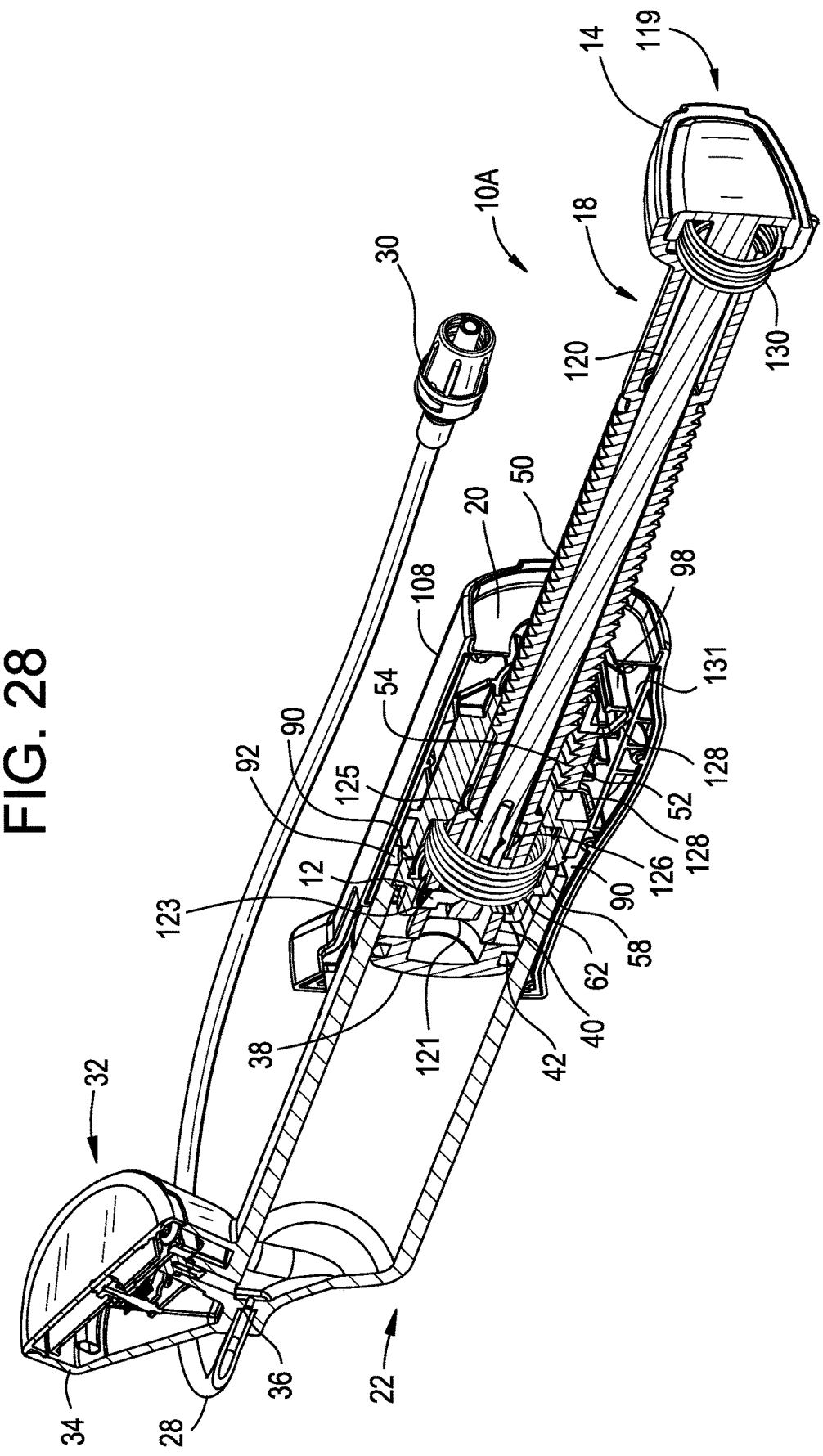
FIG. 28 is a cross-sectional view much like FIGS. 15, 18, 21 and 24, but showing the device after the vacuum therein has been released (i.e., the device in "vacuum release mode")
Figure 29:
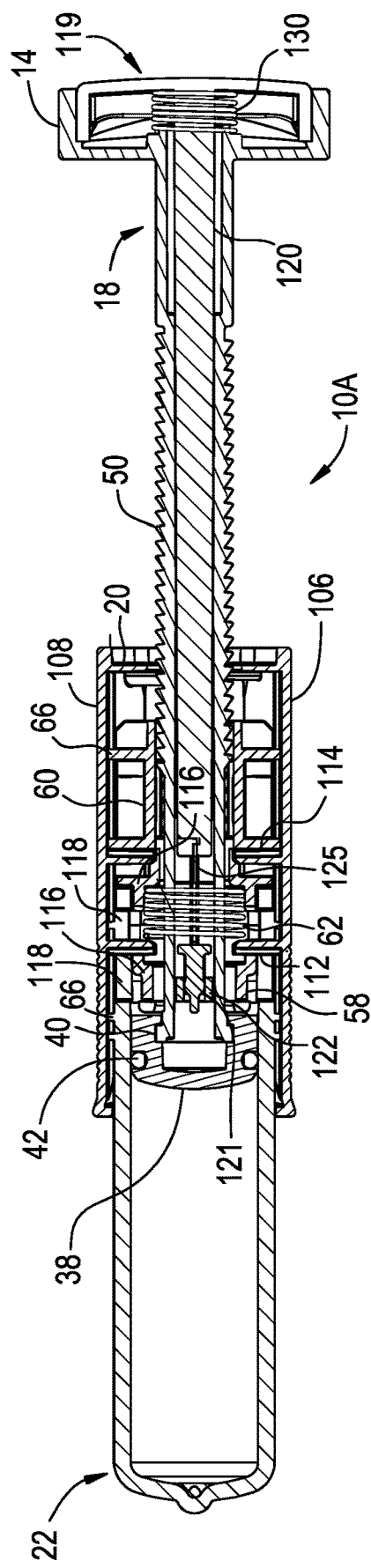
FIG. 29 is a cross-sectional view much like FIGS. 16, 19, 22 and 25, but showing the device in vacuum release mode.

Referring to FIGS. 28-29, during vacuum released mode the plunger 18 has been pulled out of the user grip assembly 16 to its fullest extent and the vacuum release button 119 has been depressed causing the latch 122 to pull into the plunger 18 and become free of the front carrier 58.

Figure 26:
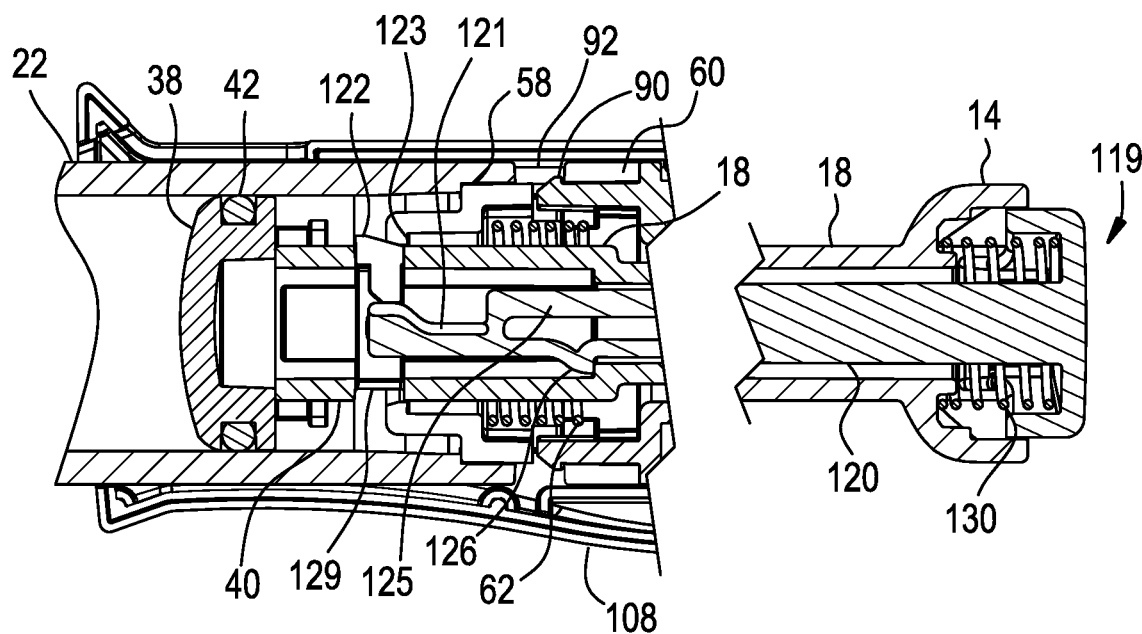
FIG. 26 is a cross-sectional view which shows a latch entering a circular ledge of a front carrier.

With regard to the position of the latch 122 during the different modes of operation of the device 10A, FIG. 26 shows the latch 122 entering the circular ledge 123 of the front carrier 58. This happens when the vacuum release button 119 is not being pressed.

Figure 27:
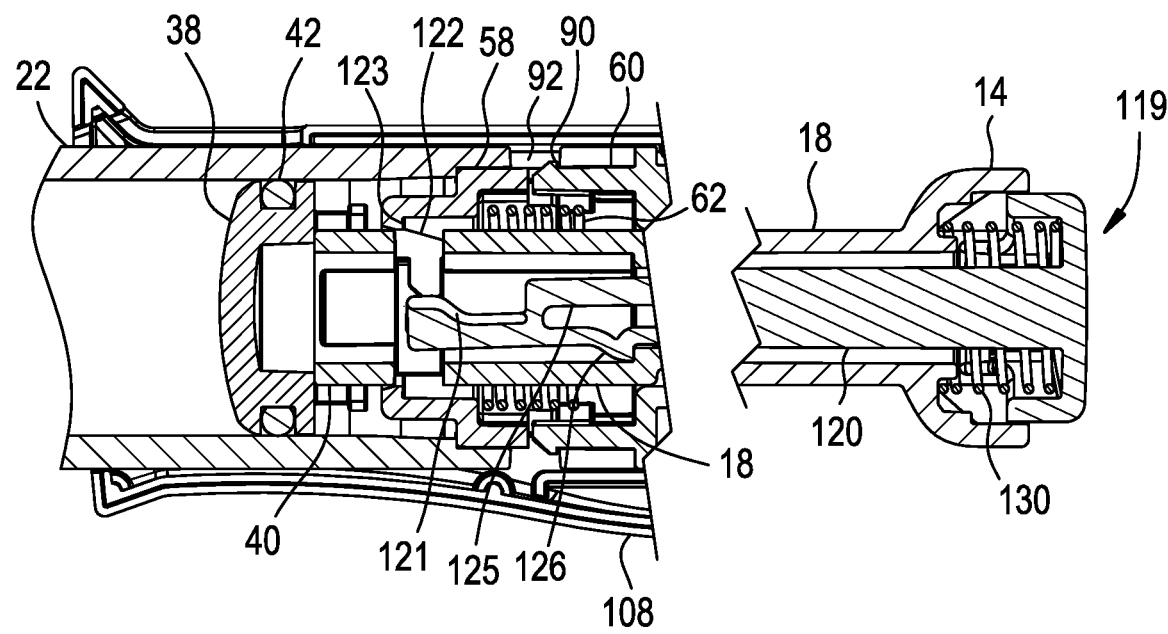
FIG. 27 is a cross-sectional view much like FIG. 26, but which shows the latch with its cam deflected under the circular ledge.

FIG. 27 shows the latch 122 with its cam deflected as latch 122 passes under the circular ledge 123. This happens when the vacuum release button 119 is not being pressed.

Figure 30:
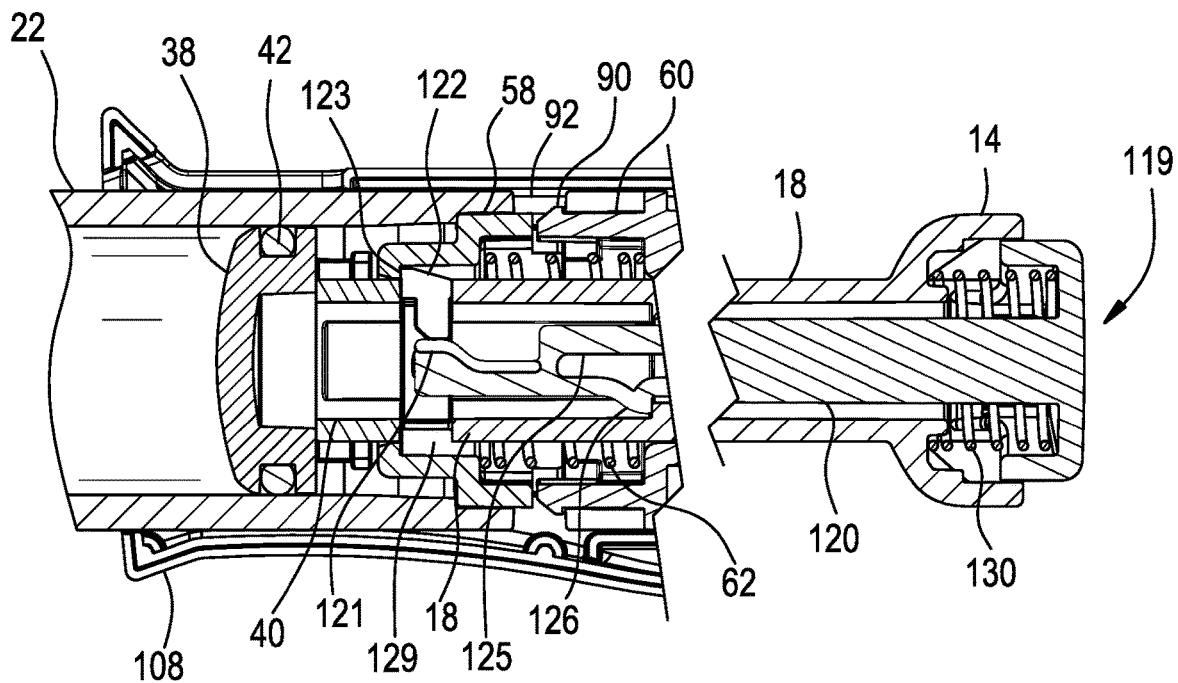
FIG. 30 is a cross-sectional view much like FIGS. 26 and 27, but which shows the position of the latch when the device is in vacuum locked mode.
Figure 31:
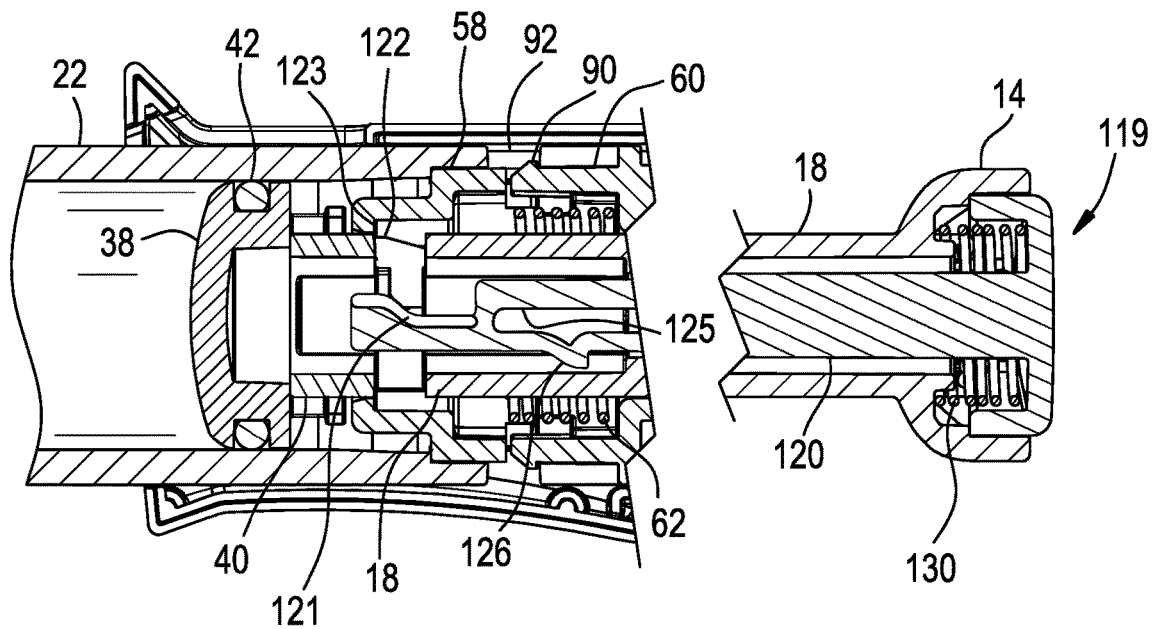
FIG. 31 is a cross-sectional view much like FIGS. 26, 27 and 30, but shows the position of the latch when the device is in vacuum release mode.

FIG. 30 shows the position of the latch 122 when the device 10A is in vacuum locked mode, while FIG. 31 shows the position of the latch 122 when the device 10A is in vacuum release mode.

One other difference between the previous device configuration (i.e., the device 10 shown in FIGS. 1-13) and the improved device (i.e., the device 10A shown in FIGS. 14-32) is that the syringe body 22 of the device 10 had to extend sufficiently to accept and enclose both the front carrier 58 and rear carrier 60. However, in order to reduce the overall length and girth of the device 10A, and to make it easier for smaller handed users to grasp the user grip assembly 16, the portion of syringe body 22 that previously enclosed the rear carrier 60 has been eliminated and the rear carrier 60 is now retained to the syringe body by alignment tabs 72 bearing latches 90. Specifically, the alignment tabs 72 slide into the opposing guide grooves 70 within the syringe body 22 and are retained in place by the engagement of latches 90 within the opposed corresponding latch slots 92. This connection between the syringe body 22 and the rear carrier 60 allows the rear carrier 60 to transfer thrust it receives from the half-nut 52, through the interaction of the thrust surface 86 and thrust face 88, to the syringe body 22.

In use, a user holds the grip assembly 16 that encloses the syringe body 22, pulls back on the plunger handle 14 which causes the syringe body 22 to pull deeper into the grip assembly 16 for a limited distance, and thereby moves the half-nut 52 into an unengaged position as shown in FIGS. 15-17. While in this position, the plunger 18—now free of the half-nut 52 and with the piston 38 attached—is thereby free to withdraw the length of the syringe body 22 and draw fluid into the syringe (i.e., into chamber 46). Both frictional drag of the piston seal ring 42 to the internal surface 44 of the syringe, and the flow resistance of the fluid being drawn into the syringe body 22, work to compress the centralization spring 62 (which provides centering when device 10A is unloaded).

When the handle 14 is released after the syringe is filled, the half-nut 52 returns to engagement as shown in FIGS. 18-20. From here, the handle 14 can be rotated by the user in order to allow the thread 50 on the plunger 18 and the thread 54 of the half-nut 52 to drive the plunger 18, by means of the screw mechanism therebetween. To discharge fluid from the syringe body 22, the user pushes the plunger 18 while holding onto the grip assembly 16. This moves the syringe body 22 outward a limited distance from within the grip assembly 16 (compressing the centralization spring 62 the opposite direction), which also disengages the thread 54 on the half-nut 52 from the thread 50 on the plunger 18 and allows the plunger 18 (with the piston 38 attached) to displace fluid from the syringe, as shown in FIGS. 21-24.

Once linear force on the plunger 18 is ceased, the centralization spring 62 brings the plunger 18 back to a neutral position in which the thread 54 on the half-nut 52 is again engaged with the thread 50 on the plunger 18, as shown in FIGS. 15-17.

From this point, the plunger 18 can be rotated by the user (using the handle 14) to utilize the mechanical advantage of the engaged half-nut 52 and plunger 18 to create high pressure within the syringe, as shown in FIGS. 18-20.

To facilitate rapid drawdown of a pressurized balloon following inflation, the user can pull the plunger 18 fully back using the handle 14 while holding the grip assembly 16. This allows the latch 122 to ride under and engage the front carrier 58 which it will catch behind in order to let the user to relax their force on the handle 14 while fluid is drawn back into the syringe from the balloon. This vacuum is maintained until all fluid is withdrawn into the syringe and the balloon is fully collapsed. Releasing the latch 122 involves pressing the release button 119 at the back of the handle 14, which pulls the latch 122 into the plunger 18 and free of the front carrier 58.

While specific embodiments of the invention have been shown and described, it is envisioned that those skilled in the art may devise various modifications without departing from the spirit and scope of the present invention.

What is claimed is:

1. A fluid pressurizing and displacement device comprising: a grip assembly having a first end and a second end; a syringe body which extends from the first end of the grip assembly; a plunger which extends from the second end of the grip assembly, said plunger having a first thread; an actuating mechanism having a second thread which is engaged with the first thread on the plunger, said actuating mechanism configured such that pushing the plunger, along with the first thread of the plunger, toward the first end of the grip assembly and toward the syringe body causes the second thread to disengage from the first thread, said actuating mechanism configured such that pulling the plunger, along with the first thread of the plunger, away from the grip assembly causes the second thread to disengage from the first thread, wherein the fluid pressurizing and displacement device is configured such that pulling the plunger away from the grip assembly fills the device with fluid, pushing the plunger toward the grip assembly purges the device of fluid, and rotating the plunger relative to the grip assembly causes the first thread on the plunger to interact with the second thread on the actuating mechanism.

2. A fluid pressurizing and displacement device as recited in claim 1, wherein the grip assembly comprises at least one cam follower, and said actuating mechanism comprises a half-nut having at least one cam thereon which interacts with said at least one cam follower providing a path of travel for the half-nut, into and out of engagement with the plunger.

3. A fluid pressurizing and displacement device as recited in claim 1, wherein the grip assembly comprises at least one cam follower, wherein the actuating mechanism comprises a half-nut comprising at least one spring finger which is configured to bias the actuating mechanism into engagement with the at least one cam follower.

4. A fluid pressurizing and displacement device as recited in claim 1, wherein the plunger comprises a longitudinal bore, further comprising a vacuum release button which comprises a shaft which extends along the longitudinal bore provided in the plunger.

5. A fluid pressurizing and displacement device as recited in claim 4, further comprising a latch, wherein the shaft comprises a distal end comprising a deflectable beam element which has a cam thereon which interacts with the latch.

6. A fluid pressurizing and displacement device as recited in claim 4, wherein the plunger comprises an internal shoulder, wherein the vacuum release button is retained within the plunger via a detent on the shaft, wherein the detent engages the internal shoulder, further comprising a vacuum release return spring which is disposed between the vacuum release button and an end of the plunger.

7. A fluid pressurizing and displacement device as recited in claim 1, further comprising a carrier assembly, said carrier assembly comprising a front carrier, a rear carrier, and a centralization spring disposed between the front carrier and the rear carrier, wherein the plunger extends through the carrier assembly.

8. A fluid pressurizing and displacement device as recited in claim 7, wherein the rear carrier defines a half-nut pocket which receives a half-nut, wherein the syringe body provides an aperture, and the half-nut operates within the aperture and the half-nut pocket in the rear carrier.

9. A fluid pressurizing and displacement device as recited in claim 8, wherein the half-nut comprises a thrust surface which engages a corresponding thrust face located in the half-nut pocket of the rear carrier.

10. A fluid pressurizing and displacement device as recited in claim 9, wherein the rear carrier is retained to the syringe body by alignment tabs bearing latches, wherein the alignment tabs slide into opposing guide grooves within the syringe body and are retained in place by the engagement of the latches within opposed corresponding latch slots.

11. A fluid pressurizing and displacement device as recited in claim 10, wherein retention between the syringe body and the rear carrier provides that the rear carrier transfers thrust it receives from the half-nut, through interaction of the thrust surface and the corresponding thrust face, to the syringe body.

12. A fluid pressurizing and displacement device as recited in claim 9, wherein the rear carrier comprises latches which engage corresponding latch slots on the syringe body, wherein thrust from the half-nut is delivered to the rear carrier via interaction between the thrust surface and the thrust face, and wherein the latches and the corresponding latch slots function to provide that the rear carrier thereafter transfers said trust to the syringe body.

13. A fluid pressurizing and displacement device as recited in claim 7, wherein the front carrier comprises a first spring pocket configured to receive a first end of the centralization spring, and the rear carrier comprises a second spring pocket configured to receive a second end of the centralization spring.

14. A fluid pressurizing and displacement device as recited in claim 7, wherein the device is configured such that the front carrier and the rear carrier are prevented from rotating in the syringe body, and define a path for travel of the carrier assembly.

15. A fluid pressurizing and displacement device as recited in claim 1, wherein said actuating mechanism comprises cams, further comprising a centralization spring, and a carrier assembly which houses the centralization spring, wherein the grip assembly comprises fingers and cam followers, wherein the fingers are positioned close enough together to serve as stops against which the centralization spring contacts in order to limit travel of the grip assembly, wherein pushing said plunger toward said grip assembly causes the cams to drive against the cam followers causing said actuating mechanism to disengage from the plunger, wherein release of the plunger causes the centralization spring to expand, wherein the cams drive against the cam followers causing said actuating mechanism to engage the plunger.

16. A fluid pressurizing and displacement device as recited in claim 1, wherein said actuating mechanism comprises cams, further comprising a piston engaged with the plunger, said piston providing a seal with a surface of the syringe body, further comprising a centralization spring, and a carrier assembly which houses the centralization spring, wherein the grip assembly comprises fingers and cam followers, wherein when the plunger is pushed or pulled relative to the grip assembly, frictional engagement of the seal with the surface of the syringe body drives the carrier assembly against the centralization spring, wherein the fingers are positioned close enough together to serve as stops against which the centralization spring contacts in order to limit travel of the grip assembly, wherein pushing said plunger toward said grip assembly causes the cams to drive against the cam followers causing said actuating mechanism to disengage from the plunger, wherein release of the plunger causes the centralization spring to expand, wherein the cams drive against the cam followers causing said actuating mechanism to engage the plunger.

\* \* \* \* \*